US012694951B2

(12) United States Patent
Yekhanin et al.

(10) Patent No.: US 12,694,951 B2
(45) Date of Patent: Jul. 28, 2026

(54) TRACE RECONSTRUCTION OF POLYMER SEQUENCES USING QUALITY SCORES

(71) Applicant: MICROSOFT TECHNOLOGY LICENSING, LLC, Redmond, WA (US)

(72) Inventors: Sergey Yekhanin, Redmond, WA (US); Amirbehshad Shahrasbi, Pittsburgh, PA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 1742 days.

(21) Appl. No.: 16/671,058

(22) Filed: Oct. 31, 2019

(65) Prior Publication Data

US 2021/0134396 A1 May 6, 2021

(51) Int. Cl.
| | |
|---|---|
| *G16B 30/00* | (2019.01) |
| *C12Q 1/6809* | (2018.01) |
| *C12Q 1/6869* | (2018.01) |
| *G06F 17/18* | (2006.01) |
| *G16B 40/10* | (2019.01) |

(52) U.S. Cl.
CPC ........... *G16B 40/10* (2019.02); *C12Q 1/6809* (2013.01); *C12Q 1/6869* (2013.01); *G06F 17/18* (2013.01); *G16B 30/00* (2019.02)

(58) Field of Classification Search
CPC .............................. C12Q 1/6869; G16B 30/00
See application file for complete search history.

(56) References Cited

U.S. PATENT DOCUMENTS

2018/0211001 A1    7/2018  Gopalan et al.

OTHER PUBLICATIONS

Robinson, Peter N., Rosario M. Piro, and Marten Jäger. "FASTQ Format." Computational Exome and Genome Analysis. Chapman and Hall/CRC, 2017. 57-65. (Year: 2017).*
Cock, Peter JA, et al. "The Sanger FASTQ file format for sequences with quality scores, and the Solexa/Illumina FASTQ variants." Nucleic acids research 38.6 (2010): 1767-1771. (Year: 2010).*

(Continued)

*Primary Examiner* — Larry D Riggs, II
*Assistant Examiner* — Guozhen Liu
(74) *Attorney, Agent, or Firm* — Benjamin Keim; Newport IP, LLC

(57) ABSTRACT

Polymeric molecules such as deoxyribose nucleic acid (DNA) provide a storage medium for digital data that has advantages over conventional storage media. Accessing digital data stored in polymers includes decoding the output of sequencers which detect the physical order of monomer subunits in the polymers. This output includes errors which are corrected through the process of trace reconstruction. Trace reconstruction identifies a consensus output sequence from a set of noisy output reads provided by a sequencer. The accuracy of trace reconstruction is improved by using weighted majority voting to determine the consensus output sequence. Weights are based on quality labels assigned by the sequencer to its output. Quality labels may be derived from empirical error data. A quality label for a single position in an output read may be determined independently or it may be influenced by quality labels of other nearby positions in the read.

20 Claims, 12 Drawing Sheets

(56)    References Cited

OTHER PUBLICATIONS

Kawano, Ryuji. "Nanopore decoding of oligonucleotides in DNA computing." Biotechnology Journal 13.12 (2018): 1800091. (Year: 2018).*

Shrivastava, Priyanka, and Uday Pratap Singh. "Error detection and correction using Reed Solomon codes." International Journal of Advanced Research in Computer Science and Software Engineering 3.8 (2013). (Year: 2013).*

Yazdi ("A rewritable, random-access DNA-based storage system." Scientific reports 5.1 (2015): 14138 (Year: 2015).*

Batu, et al., "Reconstructing Strings from Random Traces", In Proceedings of Fifteenth Annual ACM-SIAM Symposium on Discrete Algorithms, Jan. 11, 2004, 11 Pages.

Yekhanin, et al., "Non-Provisional Application as Filed in U.S. Appl. No. 16/105,349", filed Aug. 20, 2018, 72 Pages.

"Contents", https://en.wikipedia.org/w/index.php?title=FASTQ_format&oldid=923358086, Oct. 28, 2019, 10 Pages.

"Polymorphism and Genome Assembly", http://www.cs.toronto.edu/~nild/thesis_ndonmez.pdf, Nov. 1, 2012, 125 Pages.

Bhola, et al., "No-Reference Compression of Genomic Data Stored in FASTQ Format", In IEEE International Conference on Bioinformatics and Biomedicine, Nov. 12, 2011, pp. 147-150.

Laehnemann, et al., "Denoising DNA Deep Sequencing Data-High-throughput Sequencing Errors and their Correction", In Journal of Briefing in BioInformatics, vol. 17, No. 1, May 29, 2015, pp. 154-179.

"International Search Report and Written Opinion Issued in PCT Application No. PCT/US2020/056952", Mailed Date: Jan. 20, 2021, 13 Pages.

Xingyu, et al., "An Efficient Trimming Algorithm based on Multi-Feature Fusion Scoring Model for NGS Data", In Proceedings of IEEE/ACM Transactions on Computational Biology and Bioinformatics, Feb. 5, 2019, pp. 728-738.

* cited by examiner

UNWEIGHTED MAJORITY VOTING

WEIGHTED MAJORITY VOTING

600

HEAT MAP SHOWING DISTRIBUTION OF QUALITY LABELS
CONDITIONED ON THE PRECEDING QUALITY LABEL

900

ASSIGN ERROR PROBABILITIES TO THE
QUALITY LABELS
902

ASSIGN WEIGHTS TO QUALITY LABELS
904

RECEIVE A CLUSTER OF READS
906

ALIGN THE READS IN THE CLUSTER
908

EXCLUDE LOW-RELIABILITY READS FROM
THE CLUSTER    910

DETERMINE A CONSENSUS OUTPUT
SEQUENCE BY WEIGHTED MAJORITY
VOTING    912

1100

1200

TRACE RECONSTRUCTION OF POLYMER SEQUENCES USING QUALITY SCORES

BACKGROUND

Demand for data storage is growing exponentially, but the capacity of existing storage media is not keeping up. Oligonucleotides such as deoxyribose nucleic acid (DNA) are emerging as a medium for data storage. DNA is capable of storing information at high density. The theoretical density limit is 1 exabyte/mm$^3$ ($10^9$ GB/mm$^3$). Less than 100 grams of DNA could potentially store all the human-made data in the world today. DNA is also long lasting, with an observed half-life of over 500 years under certain storage conditions. Thus, DNA is appealing as an information storage technology because of its high information density and longevity.

Using oligonucleotides to store digital data requires encoding the digital data in a molecule and later recovering the digital data by reading the structure of the molecules. The zeros and ones of the digital data are represented by sequences of nucleotide bases such as adenine (A), cytosine (C), guanine (G), and thymine (T). Both the processes of creating oligonucleotides with an oligonucleotide synthesizer and later reading the sequence of those molecules with a sequencer are prone to error. Most of the errors come from sequencing. Thus, most existing encoding schemes include techniques for addressing errors introduced by sequencing and other sources in order to accurately recover digital data stored in oligonucleotides.

However, existing techniques have limits in their ability to accurately correct all errors. Some techniques sacrifice data density in order to create a more robust encoding schema. Additionally, it can be computationally very expensive for computing systems to identify and correct errors in the output from a sequencer. Accordingly, techniques that improve the accuracy of error correction of sequencer output will improve the technology of DNA data storage.

SUMMARY

This disclosure provides an improved technique for performing "trace reconstruction" that uses quality data provided by a sequencer to generate a consensus output sequence based on weighted majority voting. Trace reconstruction identifies a single nucleotide sequence, the consensus output sequence, that is most likely to represents the actual order of nucleotide bases in a nucleotide read by a sequencer. The quality data indicates how much confidence can be placed in an individual nucleotide read from a sequencer.

Trace reconstruction is used as part of the decoding process for digital data stored in oligonucleotides because the output from a sequencer is not 100% accurate. The output is often a set of multiple noisy reads for each DNA molecule read by the sequencer. The goal of trace reconstruction is to identify a "best guess" for the sequence of the original oligonucleotide molecule without knowing which, if any, of the noisy reads is correct. This process of going from many noisy reads to one, presumably accurate, consensus output sequence is trace reconstruction.

The problem of trace reconstruction assumes that m noisy reads of an oligonucleotide X denoted by $Y_1, Y_2, \ldots, Y_m$ are available and aims to recover the sequence oligonucleotide X using the noisy reads. Each noisy read may also be referred to as a "trace," thus the name trace reconstruction. Trace reconstruction provides an estimate $\tilde{X}$ ("best guess") given $Y_1, Y_2, \ldots, Y_m$. Improved trace reconstruction techniques improve the probability of the best guess being equal to the actual sequence of the oligonucleotide molecule, $Pr(\tilde{X}=X)$.

Generally, the output from an oligonucleotide sequencer includes reads representing many different oligonucleotides scrambled together. Reads that are similar to each other, and thus, were likely generated by sequencing the same oligonucleotide, can be grouped together in a cluster for further analysis. Techniques for clustering are known to those of ordinary skill in the art. One suitable clustering technique is provided in U.S. patent application Ser. No. 16/325,112 filed on Feb. 12, 2019. Once clustered, the reads may be aligned so that they can be compared to each other. Alignment of the multiple reads in a cluster may be based on the first position in the reads, the last position in the reads, and/or one or more known sequences in the reads.

Once aligned, each position in the aligned reads may be evaluated to determine which read symbol (e.g., nucleotide base call) should be included in the consensus output sequence at that position. This may be done by selecting the most common read symbol at each position through majority voting. This can be repeated for every position in the set of aligned reads to generate the consensus output sequence. At positions in which an insertion or deletion is suspected, a short window of adjacent positions may be evaluated to determine if there is an insertion or deletion. If so, the alignment of the reads is adjusted accordingly.

Techniques for creating a consensus output sequence from multiple aligned reads are known to those of ordinary skill in the art. See US Pat. Pub. No. 2018/0211001, U.S. patent application Ser. No. 16/105,349 filed on Aug. 20, 2018, and Tuğkan Batu, Sampath Kalman, Sanjeev Khanna, and Andrew McGregor. Reconstructing strings from random traces. In *Proceedings of the fifteenth annual ACM-SIAM symposium on Discrete algorithms*, pages 910-918. Society for Industrial and Applied Mathematics, 2004.

Output from oligonucleotide sequencers may include quality labels in addition to strings of reads symbols. This represents a valuable source of additional data that is ignored by other trace reconstruction techniques. Quality labels indicate a level of reliability of a given read symbol based on a determination made by the sequencer. A read symbol that is very likely to be accurate receives a higher quality label while a read symbol that is less certain is labeled with a lower quality label. Quality labels are converted to weights and the weights are used to perform weighted majority voting. Weighting based on quality labels can change the consensus output sequence in a way that improves the probability of the consensus output sequence accurately representing the sequence of the oligonucleotide molecule.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
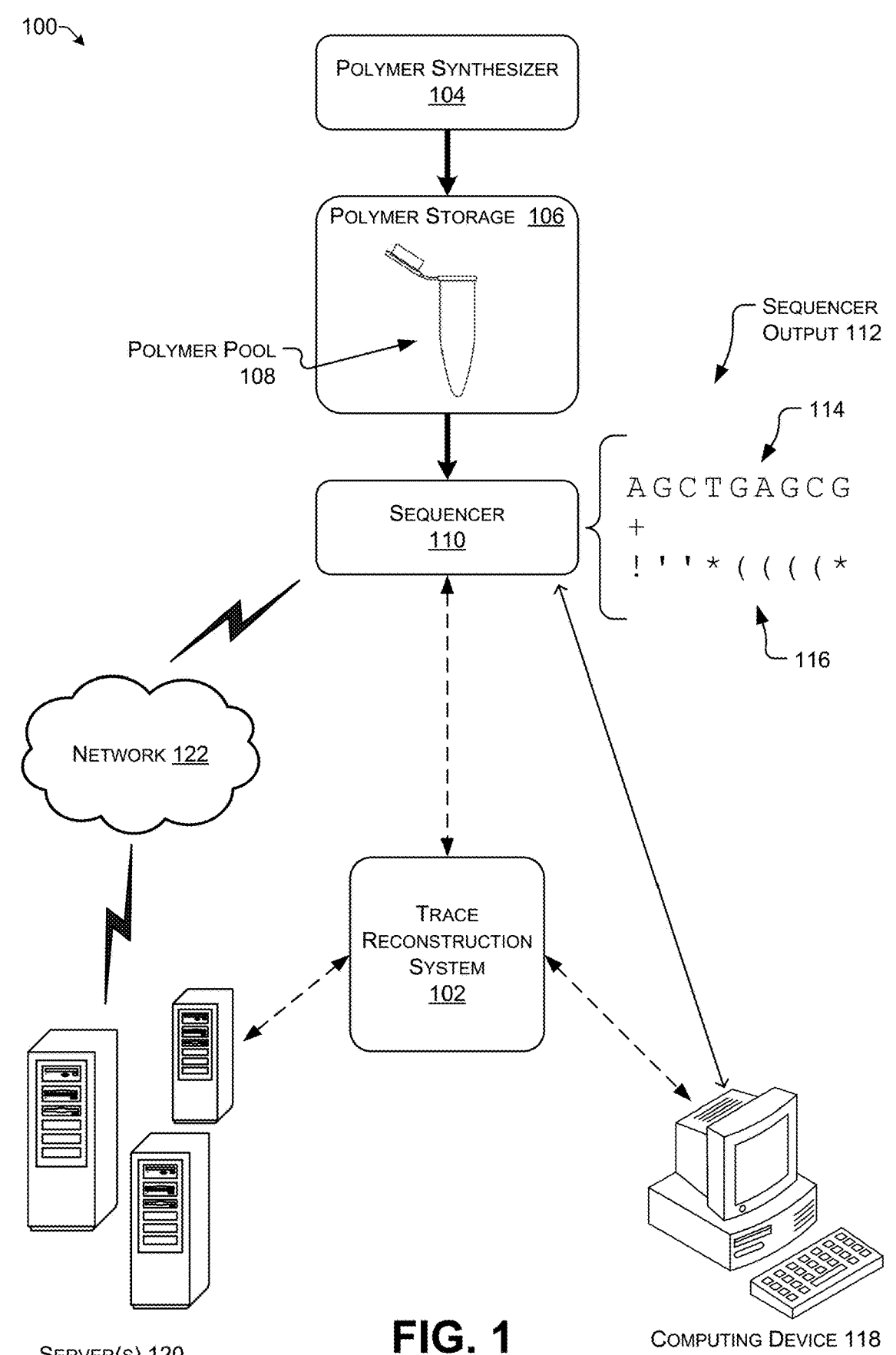
FIG. 1 shows an illustrative architecture for operation of a trace reconstruction system.

As mentioned above, oligonucleotides have great potential as a storage media for digital data. However, dealing with errors that may corrupt the data is one of the challenges of using oligonucleotides, or any polymeric molecule, to store digital data. There are many steps involved in converting digital data into oligonucleotides and then recovering the digital data from the oligonucleotides. The techniques described in this disclosure provide techniques for deriving weights from quality labels provided by an oligonucleotide sequencer and using the weights in weighted majority voting to improve the accuracy of trace reconstruction.

Currently, there are two main oligonucleotide sequencing technologies: sequencing-by-synthesis (Illumina® sequencing) and Nanopore. Although the following discussion is primarily directed to reads generated by Nanopore sequencing, the techniques provided in the disclosure are also applicable to sequencing-by-synthesis and other sequencing technologies including those yet to be developed.

Specific implementations and examples in this disclosure may refer only to oligonucleotides or specifically to DNA, but it is to be understood that the contents of this disclosure apply equally to any polymer that can encode digital data. In addition to oligonucleotides, proteins and wholly artificial polymers are examples of such polymers. As used herein, polymer refers to a molecule such as, but not limited to, an oligonucleotide. Oligonucleotide, as used herein, includes DNA, deoxyribonucleic acid (RNA), DNA-RNA hybrids, as well as oligonucleotides that include synthetic or unnatural bases.

Polymers are different from "reads" which refers to strings of data generated by a sequencer when the sequencer analyzes the chemical structure of a polymer. For example, a read may be a string of letters such as AGCT. Individual letters, or other symbol, as used in a read represent a particular type of monomer such as a specific type of nucleotide base. An individual one of these letters or symbols is referred to as a read symbol. Base calls for DNA or RNA are a specific example of reads symbols. Sequencer refers to a machine capable of detecting the physical structure of a polymer and generating a read representing that physical structure. Examples of sequencers include, but not limited to, oligonucleotide sequencers (for DNA and RNA), protein sequenators (for proteins), and electron microscopes (for many types of molecules).

Nanopore sequencing reads the sequence of nucleotide bases on a single-stranded oligonucleotide by passing the oligonucleotide through a small hole of the order of 1 nanometer in diameter (a nanopore). Immersion of the nanopore in a conducting fluid and application of a potential across the nanopore results in a slight electrical current due to conduction of ions through the nanopore. The amount of current that flows through the nanopore is sensitive to the size of the nanopore. As an oligonucleotide passes through a nanopore, each nucleotide base obstructs the nanopore to a different degree. This results in a detectable change in the current passing through the nanopore allowing detection of the order of nucleotide bases in an oligonucleotide.

FIG. 1 shows an illustrative architecture 100 for implementing a trace reconstruction system 102. Briefly, digital data that is intended for storage as DNA molecules (or alternatively as another type of polymer) is converted into information representing a string of nucleotides. The information representing the string of nucleotides (i.e., a string of letters representing an order of nucleotide bases) is provided as instructions to a polymer synthesizer 104. The polymer synthesizer 104, in this example an oligonucleotide synthesizer, chemically synthesizes a DNA molecule nucleotide by nucleotide according to the instructions. Artificial synthesis of DNA allows for creation of synthetic DNA molecules with any arbitrary sequence of nucleotide bases.

The synthetic DNA produced by the polymer synthesizer 104 may be transferred to a polymer storage 106. There are many possible ways to structure a polymer storage 106. A polymer storage 106 may be configured to include multiple physically separate regions that may each hold one or more polymer pools 108. Here example polymer pool 108 is shown as a flip top tube representing a physical container for multiple DNA molecules. DNA is generally most accessible for manipulation by bio-technological techniques when the DNA is stored in a liquid solution. Thus, the DNA pool 108 can be implemented as a chamber filled with liquid, generally an aqueous buffer, and thousands, millions, or more individual DNA molecules may be present.

In addition to a liquid suspension, DNA can be stored in a glassy (or vitreous) state, as a lyophilized product, as part of a salt, adsorbed on the surface of a nanoparticle, or another format. The structure of the polymer pools 108 may be implemented as any type of mechanical, biological, or chemical arrangement that confines a volume of liquid including the polymers to a physical location. Storage may also be in a non-liquid form such as a solid bead or by encapsulation. For example, a flat surface having a droplet present thereon, with the droplet held in place by surface tension of the liquid is one implementation of a polymer pool 108.

DNA removed from the polymer storage 106 may be sequenced with a sequencer 110. In some implementations, DNA strands may be prepared for sequencing by amplification using polymerase chain reaction (PCR) to create a large number of DNA strands that are copies of each other. While PCR amplification does introduce some errors (i.e., the copies are not all identical), the error rate of PCR is much lower than the error rate of sequencing. The need for PCR amplification prior to sequencing may depend on the specific sequencing technology used. In other implementations, such as single molecule sequencing, PCR amplification is unnecessary.

As mentioned above, the sequencer 110 reads the order of nucleotide bases in a DNA strand and generates one or more reads from that strand. Polynucleotide sequencers 110 use a variety of techniques to interpret molecular information and introduce errors into the data in both systematic and random ways. The errors introduced by sequencing are of the form of edit operations that can be categorized as substitution errors, insertion errors, and deletion errors. With substitution errors, the correct nucleotide is misread leading to an incorrect base call. Insertion errors add an additional base call although there is no nucleotide at that position in the actual molecule. Deletion errors result when the sequencer 110 fails to detect a nucleotide that exists in the DNA strand.

The sequencer 110 provides sequencer output 112. The sequencer output 112 includes one or more reads 114 and quality labels 116 indicating a level of confidence for individual read symbols (e.g., base calls) in the read. The sequencer output 112 may be provided as an electronic file such as a text file, HTML file, or other type of electronic file. One file format that is common for storing biological sequence data is the FASTQ format. FASTQ format is a text-based format for storing both a biological sequence (usually oligonucleotide sequence) and its corresponding quality labels. In FASTQ format, both the nucleotides and quality labels are each encoded with a single ASCII character for brevity. The characters representing quality labels run from 0x21 (lowest quality; '!' in ASCII) to 0x7e (highest quality; '~' in ASCII).

For some sequencing technology, the quality labels may correlate with percentages or probabilities of accuracy such as Phred quality scores. However, for other sequencing technology the quality labels are simply a ranking that is not associated with any numerical probabilities. Quality labels for Nanopore sequencing data provides a rank order of quality, but unlike Phred quality scores, these quality labels do not provide a numerical probability of error. Intuitively, a lower quality label indicates a higher probability of error and a higher quality label indicates a lower probability of error.

The quality labels in FASTQ format using ASCII symbols may be mapped to sequential integers making it easier to understand the ordering of the quality labels. Table 1 below provides a quality label mapping from ASCII symbols to numerical ranks.

TABLE 1

| ASCII quality labels from FASTQ formatted data mapped to integer rankings where 0 is the lowest ranking and 94 is the highest ranking. | |
| --- | --- |
| ASCII Label | Rank |
| ! | 0 |
| " | 1 |
| # | 2 |
| $ | 3 |
| % | 4 |
| & | 5 |
| ' | 6 |
| ( | 7 |
| ) | 8 |
| * | 9 |
| + | 10 |
| , | 11 |
| − | 12 |
| . | 13 |
| / | 14 |
| 0 | 15 |
| 1 | 16 |
| 2 | 17 |
| 3 | 18 |
| 4 | 19 |
| 5 | 20 |
| 6 | 21 |
| 7 | 22 |
| 8 | 23 |
| 9 | 24 |
| : | 25 |
| ; | 26 |
| < | 27 |
| = | 28 |
| > | 29 |
| ? | 30 |
| @ | 31 |
| A | 32 |
| B | 33 |
| C | 34 |
| D | 35 |
| E | 36 |
| F | 37 |
| G | 38 |
| H | 39 |
| I | 40 |
| J | 41 |
| K | 42 |
| L | 43 |
| M | 44 |
| N | 45 |
| O | 46 |
| P | 47 |
| Q | 48 |
| R | 49 |
| S | 50 |
| T | 51 |
| U | 52 |
| V | 53 |
| W | 54 |
| X | 55 |
| Y | 56 |
| Z | 57 |
| | 58 |
| [ | 59 |
| \ | 60 |
| ] | 61 |
| /\ | 62 |
| _ | 63 |
| ` | 64 |
| a | 65 |
| b | 66 |
| c | 67 |
| d | 68 |
| e | 69 |
| f | 70 |
| g | 71 |
| h | 72 |
| i | 73 |

TABLE 1-continued

ASCII quality labels from FASTQ formatted data
mapped to integer rankings where 0 is the lowest
ranking and 94 is the highest ranking.

| ASCII Label | Rank |
| --- | --- |
| j | 74 |
| k | 75 |
| l | 76 |
| m | 77 |
| n | 78 |
| o | 79 |
| p | 80 |
| q | 81 |
| r | 82 |
| s | 83 |
| t | 84 |
| u | 85 |
| v | 86 |
| w | 87 |
| x | 88 |
| y | 89 |
| z | 90 |
| { | 91 |
| | | 92 |
| } | 93 |
| ~ | 94 |

The rank ordering of quality labels shown in Table 1 is useful for identifying the relative accuracy of read symbols in a read of a polymer sequence but does not directly provide a numerical value for use in weighted majority voting. The quality labels 116 in the sequencer output 112 may be correlated with error rates through techniques described in further detail below such as empirical measurement of errors present in sequencer output 112 generated from a known sequence.

The sequencer output 112 is provided to the trace reconstruction system 102. The trace reconstruction system 102 may be implemented as an integral part of the sequencer 110. The sequencer 110 may include an onboard computer that implements the trace reconstruction system 102. Alternatively, the trace reconstruction system 102 may be implemented as part of a separate computing device 118 that is directly connected to the sequencer 110 through a wired or wireless connection that does not cross a network. For example, the computing device 118 may be a desktop or notebook computer used to receive data from and/or to control the sequencer 110. A wired connection may include one or more wires or cables physically connecting the computing device 118 to the sequencer 110. The wired connection may be created by a headphone cable, a telephone cable, a SCSI cable, a USB cable, an Ethernet cable, FireWire, or the like. The wireless connection may be created by radio waves (e.g., any version of Bluetooth, ANT, Wi-Fi IEEE 802.11, etc.), infrared light, or the like.

The trace reconstruction system 102 may also be implemented as part of a cloud-based or network system using one or more servers 120 that communicate with the sequencer 110 via a network 122. The network 122 may be implemented as any type of communications network such as a local area network, a wide area network, a mesh network, an ad hoc network, a peer-to-peer network, the Internet, a cable network, a telephone network, and the like. Additionally, the trace reconstruction system 102 may be implemented in part by any combination of the sequencer 110, the computing device 118, and the servers 120.

Figure 2:
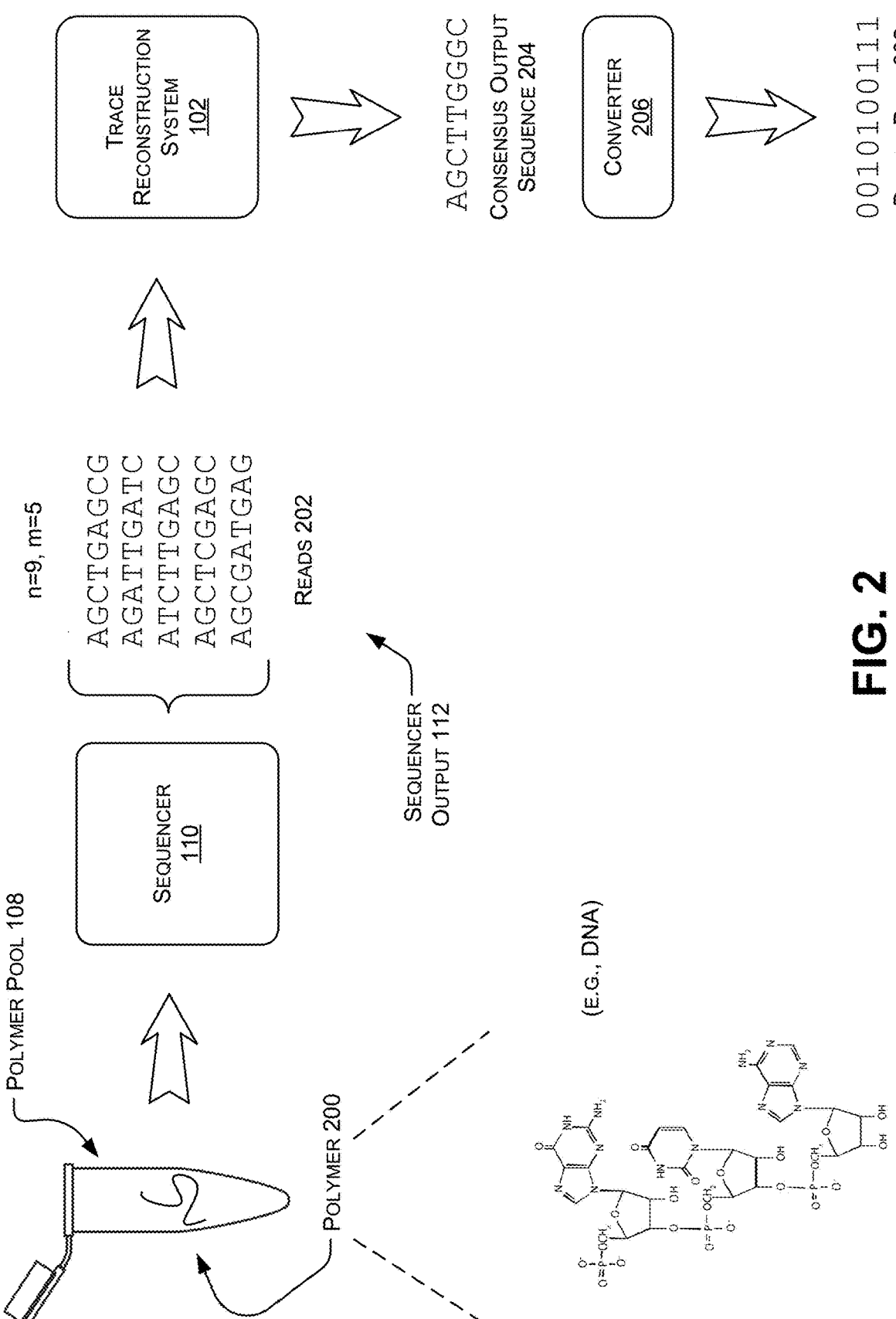
FIG. 2 is an illustrative schematic showing the use of a trace reconstruction system.

FIG. 2 shows the use of the trace reconstruction system 102 as part of the process of decoding information stored in a polymer 200 such as a synthetic DNA molecule. The polymer 200 has a specific sequence of monomer subunits (e.g., nucleotide bases). The polymer 200 may be stored in the polymer pool 108 shown in FIG. 1. The sequencer 110 produces a sequence output 112 that includes multiple noisy reads 202 each representing, with their respective errors, the sequence of monomers in the polymer 200. The number of reads may be related to coverage depth of the sequencing. Greater depth of sequencing leads to, on average, more sequences generated from each polymer 200. Because of the errors in sequencing, it is likely that many of the multiple reads have different sequences.

Each of the reads has a length (n) which in this example is nine corresponding to nine bases in a DNA strand. In actual sequence data the noisy reads may have different lengths that are not all equal to each other. Deletions and insertions are one cause of variation in read length. Locations on a read may be referred to as "positions" such as in this example going from position one to position nine. As used herein, "base" refers to a location of a given monomer in a DNA molecule while "position" refers to a location along a string of data such as a read. Thus, assuming no errors, the third base in a DNA molecule corresponds to the third position in a read generated by the sequencer 110.

The number (m) of noisy reads 202 provided to the trace reconstruction system 102 is five in this example. However, there may be more or fewer reads. The number of noisy reads 202 provided to the trace reconstruction system 102 may be less than the total number of reads produced by the sequencer 110. A subset of the total number reads produced by the sequencer 110 may be selected at random or using heuristics for analysis by the trace reconstruction system 102. In addition to random selection, other techniques may be used for choosing which subset of reads are passed to the trace reconstruction system 102. For example, quality information may be used to identify m reads having the highest overall reliability from all of the reads generated by the sequencer 110. In some implementations, only reads with certain lengths are selected.

The trace reconstruction system 102 analyzes the noisy reads 202 according to the techniques of this disclosure and generates a consensus output sequence 204. There are many possible techniques for generating because of the consensus output sequence 204 from a plurality of noisy reads 202. The consensus output sequence 204 represents the "best guess" of the trace reconstruction system 102 for the actual sequence of the polymer 200. The consensus output sequence 204 may be generated in part by majority voting including weighted majority voting in which the weights are derived from the quality labels.

A converter 206 converts the consensus output sequence 204 into digital data 208, thereby retrieving the digital information stored in the polymer 200. The converter 206 may use additional error correction techniques (e.g., Reed-Solomon error correction) to correct any remaining errors in the digital data 208. Thus, it is not necessary for the trace reconstruction system 102 to correct all types of errors because there are opportunities to apply additional error correction techniques.

Figure 3:
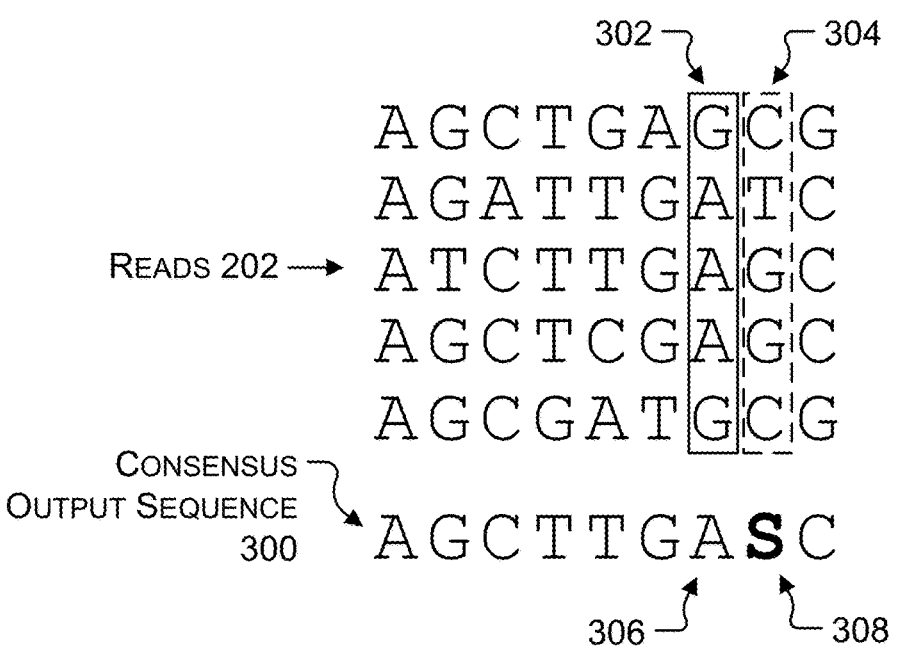
FIG. 3 shows a comparison consensus output sequences generated from unweighted majority voting and from weighted majority voting according to the techniques of this disclosure.
Figure 3:
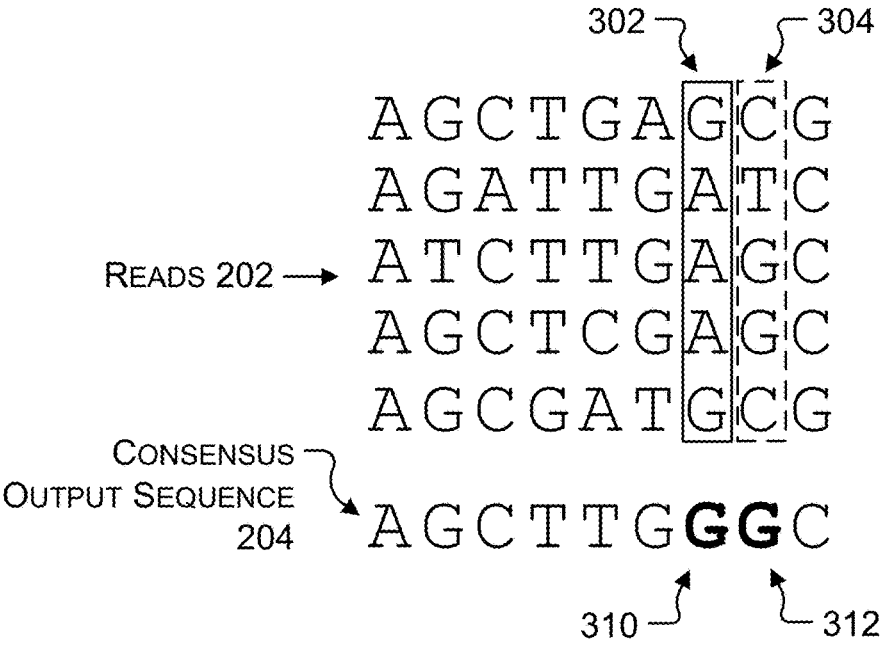

FIG. 3 compares unweighted majority voting and weighted majority voting as techniques for determining a consensus output sequence 300, 204 from a plurality of noisy reads 202. The noisy reads 202 may be a subset of all the reads present in the sequencer output 112 that are grouped into a single cluster based on similarly to each other by any known clustering technique. Clustering creates a group of reads 202 that, due to their similarity, likely represent different readings of the same polymer 200. The reads 202 may be aligned at a starting position, and ending position, or any position shared across all of the reads 202. The starting position may correspond to the 5' end of an oligonucleotide and that ending position may correspond to the 3' end of an oligonucleotide. In the figures of this disclosure the 5' end is oriented to the left.

A first position of comparison 302 spanning the reads is represented by the solid rectangular box. A second position of comparison 304 spanning the reads is represented by the dashed rectangular box. Majority voting identifies which nucleotide or other type of read symbol is most common across all of the reads 202 at a position of comparison. Using unweighted majority voting, at the position of comparison 302 the most numerous base call is A so the consensus output read symbol 306 for this position is A.

At the position of comparison 304, there are an equal number of C and G base calls so unweighted majority voting is unable to identify a single base call for this position. This may be handled, in some implementations, by using an ambiguous consensus output read symbol 308 at this position. In this example, the consensus output read symbol 308 is S representing "strong" meaning either C or G. The potential for ties is one characteristic of unweighted majority voting. The consensus output sequence 300 generated from unweighted majority voting in this example is AGCTT-GASC.

Weighted majority voting uses weights derived from error probabilities to bias votes with higher confidence. Thus, not only the number of base calls for each type of nucleotide at a position of comparison but also the relative confidence in those base calls as represented by error probabilities are used to determine a consensus output read symbol. Thus, the consensus read symbol for a given position of comparison is the read symbol with the maximum total weight. At the position of comparison 302, in this example the error probabilities for the three base calls of A are higher than the error probabilities for the two base calls G. Weighting the five separate base calls at the position of comparison 302 results in the two G base calls having a higher total score than the three A base calls. Therefore, the consensus output read symbol 310 at this position is G rather than A in the consensus output sequence 300 generated by unweighted majority voting.

At the position of comparison 304, the presence of two C base calls and two G base calls resulted in a tie using unweighted majority voting. In this example, the combined error probabilities for the two G base calls are lower than the error probabilities for the two T base calls resulting in G receiving more "votes." Thus G is selected as the consensus output read symbol 312 for this position of comparison 304.

There are many conceivable ways in which quality labels could be converted into weights. One way would be simply to use the numerical rank order of the integer quality labels as the weight. For example, the ASCII quality label "+" has the integer quality label "10" and the ASCII quality label "5" has the integer quality label "20" in Table 1 above. Thus, any base call with the ASCII quality label 5 would be given twice the weight of a base call with the "+" quality label. While simple and perhaps intuitively appealing, empirical data discussed later shows that this way of weighting quality labels is not optimal. Another possible way to generate weights for the weighted majority voting would be to use the probability of accuracy as the weight. For example, if a base call has a 10% error probability then it would have a 90% probability of accuracy and that base call may receive a weight of 0.9. However, the analysis provided below suggests using a weighting factor derived from error probabilities rather than using error probabilities directly as weights.

The technique used for determining weights in this disclosure involves a more sophisticated consideration of the probability of a given base call with respect to each of the possible nucleotide bases. The number of votes at a given position of comparison for nucleotide bases A, C, G, T can be represented as $n_A$, $n_C$, $n_G$, and $n_T$. The alphabet of choices for the votes (i.e., A, C, G, and T) will of course change depending on the number and types of monomers used in the polymer. The error probability for $n_i$ votes to symbol $i \in$ A, C, G, T is $$P_1^i, P_2^i, \dots P_{n_i}^i.$$

These probabilities are found by mapping the quality labels to error probabilities. Examples of empirical techniques for identifying such mappings are described in greater detail below. With these probabilities, the likelihood of the actual base being $i \in$ A, C, G, T is $$\left(1 - P_1^i\right)\left(1 - P_2^i\right)\dots\left(1 - P_{n_i}^i\right) \prod_{i' \in \{A,C,G,T\}\backslash\{i\}} P_1^{i'} P_2^{i'} \dots P_{n_{i'}}^{i'} \qquad \text{Eqn. (1)}$$

since all votes to i were correct, events that happens with probability $$1 - P_j^i$$

and all votes to i'≠i were incorrect, events that happen with probability $$P_j^{i'}.$$

Assuming the accuracy of the model and corresponding error probabilities, one technique is to choose the symbol $i \in \Sigma = \{A, C, G, T\}$ that maximizes the likelihood in Equation (1). Note that i has a higher likelihood than $j \in \Sigma\backslash i\}$ if and only if $$\left(1 - P_1^i\right) \dots \left(1 - P_{n_i}^i\right) P_1^j \dots P_{n_j}^j \geq \left(1 - P_1^j\right) \dots \left(1 - P_{n_j}^j\right) P_1^i \dots P_{n_i}^i$$

$$\Leftrightarrow \prod_{k=1}^{n_i} \frac{1 - P_k^i}{P_k^i} \geq \prod_{k=1}^{n_j} \frac{1 - P_k^j}{P_k^j}$$

$$\Leftrightarrow \sum_{k=1}^{n_i} \log \frac{1 - P_k^i}{P_k^i} \geq \sum_{k=1}^{n_j} \log \frac{1 - P_k^j}{P_k^j}$$

Accordingly, this indicates that log $$\frac{1 - P_s}{P_s}$$

should be used as the weight for vote with quality label s where $P_s$ is the probability of a symbol with quality label s being erroneous. Accordingly, implementations described in this disclosure apply a weight of log $$\frac{1 - P_s}{P_s}$$

to any vote with quality label s. For example, if a quality label s has an error probability of 7%, then the weight is determined by log $$\frac{1 - 0.07}{0.07} = \log 13.286 = 1.123.$$

Figure 4:
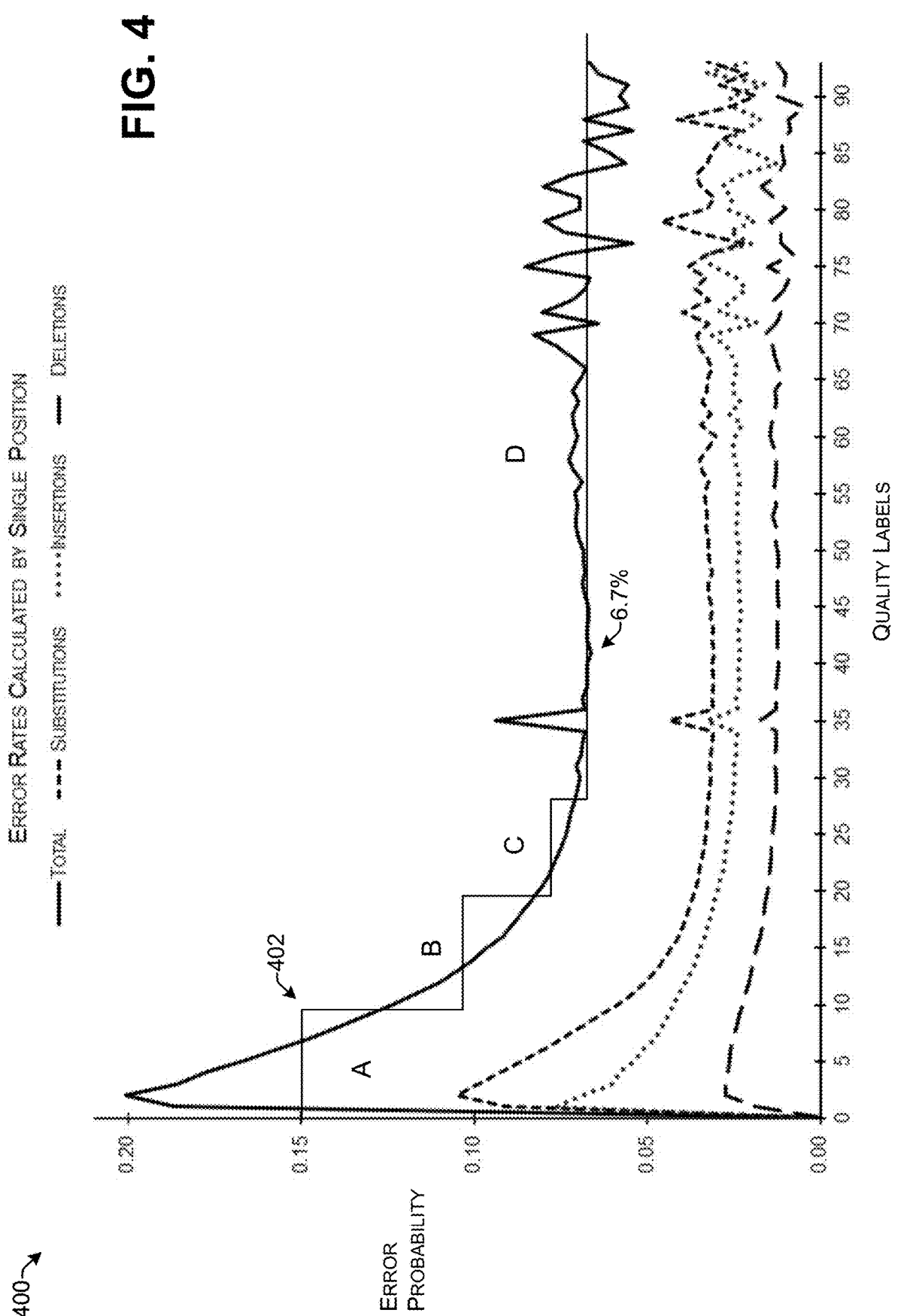
FIG. 4 is a graph showing an empirically determined correlation between quality labels and error probability for Nanopore sequencing calculated by counting errors at individual nucleotide positions separately.

FIG. 4 shows a graph 400 of empirically measured error rates for Nanopore sequencing. Error labels generated by Nanopore sequencers are ordered from low-quality to high-quality but are not currently associated with error probabilities. Thus, there is no direct way to use an ASCII quality label such as "*" as a weight in weighted majority voting. Graph 400 provides a correlation between a quality label and an error probability. Error probability is determined by counting, for each quality label, the number of substitution, deletion, and insertion errors and dividing that by the total number of base calls. This yields an error probability such as, for example, 0.1 indicating that 1 in 10 of the bases with that quality label have some type of error. The quality labels are shown as sequentially numbered integers based on the mapping from Table 1.

The data shown in graph 400 and other graphs in this disclosure are derived from a data set of Nanopore sequencing data in which the actual sequences of the DNA molecules are known. The specific error rates may be different for a different data set, but without being bound by theory, it is believed that the error rates are representative of current Nanopore sequencing technology. In this dataset, the quality label 35 is associated with a spike in error rates. There is an apparent artifact in the data.

As is apparent by examination of graph 400, the error probability for the lowest quality error labels is much higher than for other quality labels. Also, for the highest quality labels, which occur infrequently in Nanopore sequencer output, the error appears to include significant noise. Excluding the noisy, high-quality labels, the lowest error probability in this dataset is 0.067 or 6.7%. Using the relationship shown by graph 400, an error probability may be assigned to each quality label.

The relationship shown by graph 400 may be simplified by binning or grouping sets of quality labels so that all the quality labels any given group are assigned the same error probability. One possible configuration of grouped quality labels is shown by line 402. In this example configuration, group A is assigned an error probability of 0.15 and includes quality labels 0-8, group B is assigned an error probability of 0.11 and includes quality labels 9-18, group C is assigned an error probability of 0.08 and includes quality labels 19-28, and group D is assigned an error probability of 0.067 and includes all quality labels 29 and higher.

Of course, the data may be divided into a larger or smaller number groups and the error probabilities assigned to each group may be different than those used in this example. In one variation of this binning technique, one or more of the lowest quality labels (i.e., labels: 0, 1, 2) may be assigned an error probability of 1 effectively giving them a weight of zero and excluding them from the determination of a consensus output sequence. Simplifying the relationship shown by graph 400 by binning or grouping quality labels way can eliminate artifacts (e.g., quality label 35) and noise that affects the error probabilities of the higher quality labels (e.g., 60-94).

This type of binning or grouping technique may also be applied to only a part of the data represented in graph 400. For example, because the quality labels increase in quality as the numeric integer labels increase in value, it is reasonable to assume that, absent noise, graph 400 would have an asymptotic tail to the right. Stated differently, it is unlikely that quality label 74 has a higher error probability than quality label 29. To account for this noise with the high-quality labels, the lowest error probability identified for the lowest quality half of the quality labels may be assigned to all of the highest quality half of the quality labels. Thus, in this example, the error probability of 0.067 would be assigned to quality labels 46 and higher. In a variation of this technique, the lowest error probability identified for any quality label in the lowest quality half of the quality labels, is assigned to all higher quality labels. For example, the error probability of 0.067 identified a quality label 40 would then also be applied to quality labels 41-94.

Figure 5:
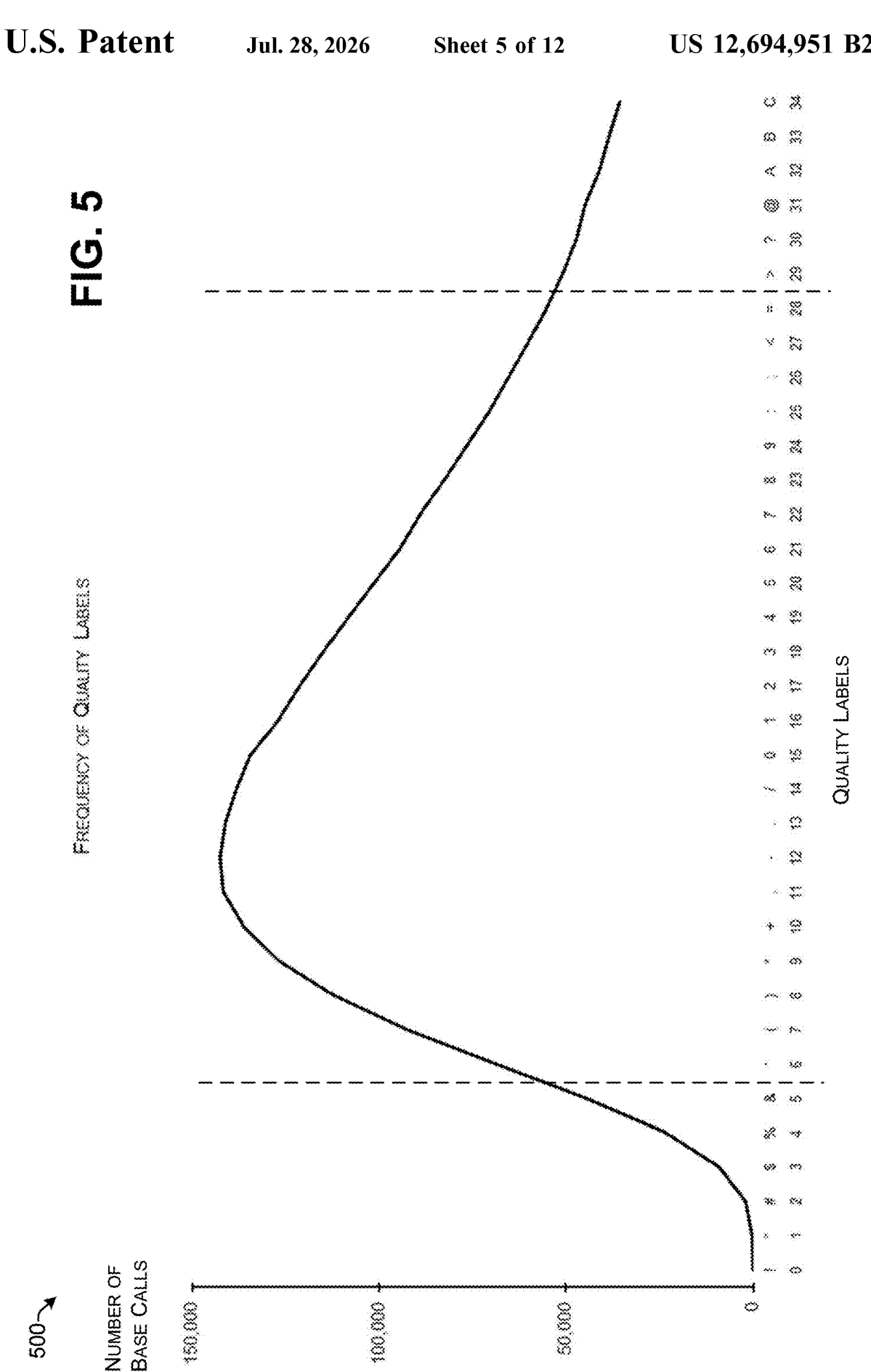
FIG. 5 is a graph showing a distribution of frequency of quality labels applied to base calls in a set of Nanopore sequence data.

FIG. 5 shows a graph 500 of the frequency of quality labels in FASTQ files generated by Nanopore sequencing. Graph 500 shows that the bulk of the base calls have quality labels in the range of about 6-28. To reduce the width of the graph, Graph 500 only shows the frequency of quality labels up to quality label 34. Frequency of quality labels greater than 34 continues decreasing on the same trend shown in graph 500. This low occurrence of the higher quality labels creates smaller sample sizes, and thus, is likely the reason for greater noise in the error probability data shown in FIG. 4.

Figure 6:
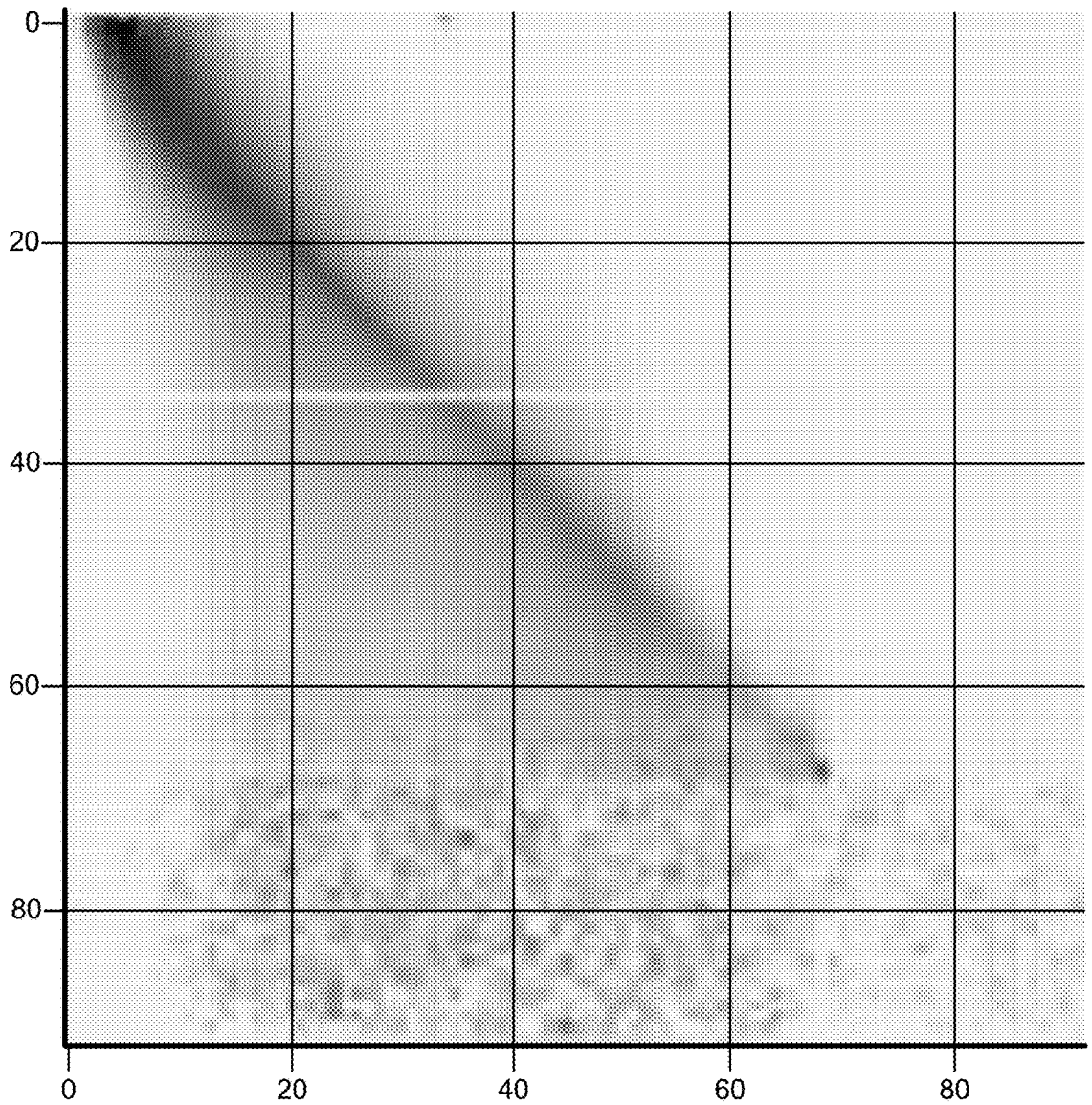
FIG. 6 is a heat map showing correspondence between the quality label for a given base call and the quality label for an adjacent base call.

FIG. 6 shows a heat map 600 illustration correlation between quality labels assigned to adjacent base calls. In nanopore sequenced strands the quality labels between close-by bases are highly correlated. In fact, knowing the quality label of a certain base drastically changes the distribution of the quality label at the following position. This may be thought of as the "stickiness" of a quality label. A quality label at a given position is "sticky" in that it keeps nearby quality labels at a similar level of quality.

The vertical axis shows quality labels for a base call ranging from 0 to 94. The horizonal axis shows, for all base calls with that quality label in the dataset, the distribution of quality labels of the preceding base. Darker coloration on the heat map represents increased frequency. Thus, heat map 600 shows for a base call with a quality label of 20, the distribution of the quality labels for the preceding base call is clustered around 20. A similar relationship for other quality labels is shown by the diagonal dark line. The artifact in the data for the quality label of 35 appears as a horizontal white line. The diagonal dark line disappears around quality label 68 presumably due to the noise present in the higher quality read symbols.

Figure 7:
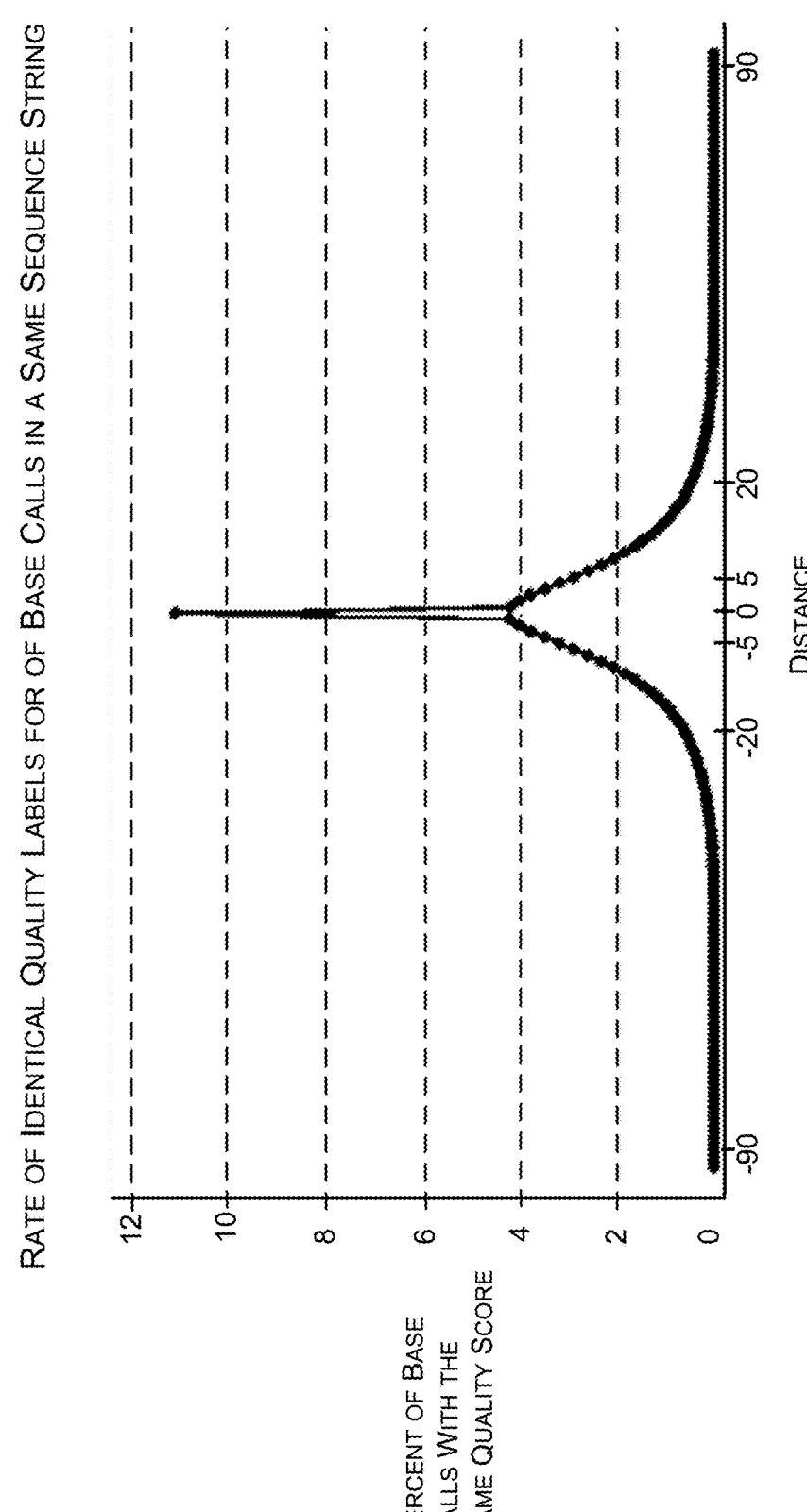
FIG. 7 is a graph showing a relationship between a distance of two base calls in a sequence string and the rate of identical quality labels.

FIG. 7 shows a graph 700 of the probability of the same rank-ordered quality label on two separate base calls. Graph 700 illustrates the same "stickiness" of quality labels shown in the heat map 600. However, graph 700 shows the relationship between quality labels not only of adjacent bases calls as in FIG. 6 but also for greater distances. Without being bound by theory, it is believed that this behavior stems from the fact that error introduced by Nanopore sequencing tends to come in bursts. Also, Nanopore sequencers perform sequencing in a block-by-block fashion which may contribute to the observed correlation in quality labels between near-by base calls.

The horizontal axis of graph 700 indicates the distance between a first base call in a sequence string and a second base call in the same sequence string. A distance of 0 at the center of the graph 700 indicates that the first base call and the second base call are consecutive. A distance of 5 indicates that the first base call comes five positions before the second base call (e.g., there are four other base call in between), and so forth. The vertical axis shows the percentage of base call with the same quality label. Thus, graph 700 shows that 11% of consecutive base calls (0 on the horizontal axis) have the same quality label. The percentage of base calls with the same quality score decreases rapidly as distance increases and at a distance of ±20 it is about 0.5 percent.

The relationship between the quality label for given base call and the quality labels for other base calls in the same vicinity suggests that it may be better to also consider the quality labels of adjacent bases not just the quality label of the base in isolation. This can be done by creating a "neighborhood" quality label based on the quality labels from all the base calls in a window that includes the base call of interest. The size of the window or the "neighborhood" is arbitrary and it may include three, five, seven, or a different number of base calls. In one example, the window includes the base call interest and two other base calls on either side for a total of five base calls. The weight assigned to the base call in the middle of this window may be the average weight for all of the base calls within the window.

Table 2 below shows the strength of correlation between base calls separated by distance d for various d≥1.

TABLE 2

Shows the strength of correlation between a quality label for a first base call and a quality label for a second base call that appears d units afterwards.

| Distance (d) | Correlation |
|---|---|
| 1 | 0.6526315 |
| 2 | 0.5253992 |
| 3 | 0.4076888 |
| 4 | 0.3376741 |
| 5 | 0.2688178 |
| 6 | 0.2480546 |
| 7 | 0.2351567 |
| 8 | 0.2247878 |
| 9 | 0.214136 |
| 10 | 0.2097247 |
| 20 | 0.1966385 |
| 30 | 0.1920138 |
| 40 | 0.1872217 |
| 0 | 0.1837144 |
| 75 | 0.1702032 |
| 100 | 0.1640558 |

Correlation is a measure of statistical association between two variables and is defined as their covariance divided by the product of their standard deviations. The correlation is zero if two variables are independent. With Nanopore sequencer output there is a strong correlation for nearby base calls. The strength of correlation decreases as the distance increases but event at a distance of 100 there is still a correlation of over 0.16.

Figure 8:
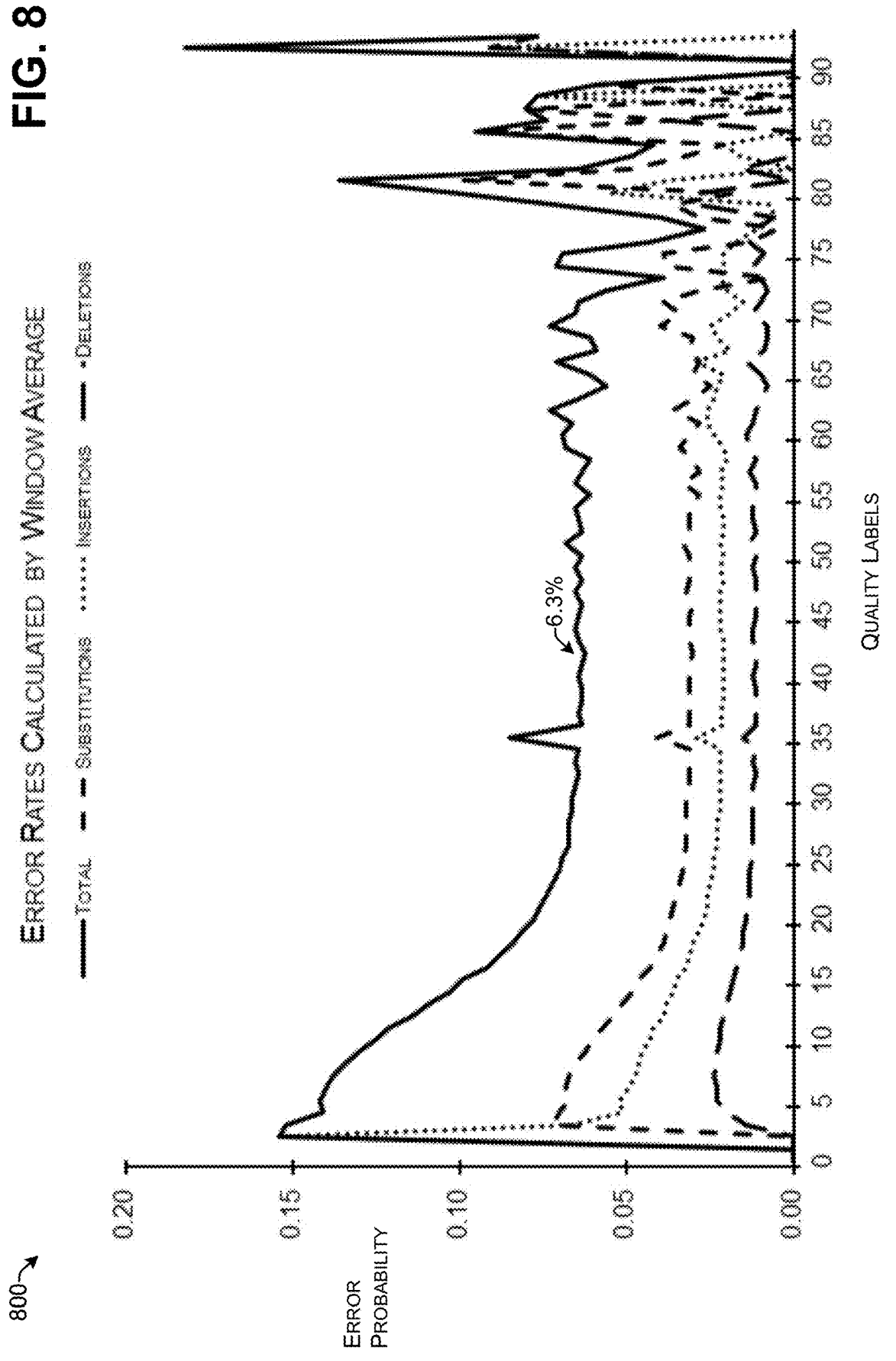
FIG. 8 is a graph showing an empirically determined correlation between quality labels and error probability for Nanopore sequencing calculated by considering the quality labels of a window including multiple adjacent nucleotide positions.

FIG. 8 shows a graph 800 of empirically measured error rates for Nanopore sequencing. Graph 800 differs from graph 400 in that the error rate for each quality label is based on an average of error rates over a window of base calls. This technique for determining error probabilities is suggested by the correlation between the quality labels of near-by base calls. Instead of computing weights using the error probabilities that are obtained by the quality label of a single base, the error probabilities are derived from the error probability of the base call itself and several (e.g., two, four, six) base calls surrounding it. In one implementation, the window is a symmetric neighborhood centered around the base call being evaluated.

One technique calculates an average error probability for all the base calls in a window and assigns that error probability to the base call in the middle of the window. The quality label for the $i^{th}$ base call is denoted by $s_i$. Error probabilities for deletion, insertion, and substitution errors may be calculated using the following formulas.

$$\Pr\left\{ \text{Deletion at Base Call } i \,\middle|\, \left\lfloor \frac{s_{i-2} + s_{i-1} + s_i + s_{i+1} + s_{i+2}}{5} \right\rfloor = x \right\} = P_x^{del}$$

$$\Pr\left\{ \text{Insertion at Base Call } i \,\middle|\, \left\lfloor \frac{s_{i-2} + s_{i-1} + s_i + s_{i+1} + s_{i+2}}{5} \right\rfloor = x \right\} = P_x^{ins}$$

$$\Pr\left\{ \text{Substitution at Base Call } i \,\middle|\, \left\lfloor \frac{s_{i-2} + s_{i-1} + s_i + s_{i+1} + s_{i+2}}{5} \right\rfloor = x \right\} = P_x^{sub}$$

and in the weighted majority voting log $$\frac{1 - P_s}{P_s}$$

can be used as the weight for base call at i where $$s = \left\lfloor \frac{s_{i-2} + s_{i-1} + s_i + s_{i+1} + s_{i+2}}{5} \right\rfloor$$

and $$P_s = P_s^{del} + P_s^{ins} + P_s^{sub}.$$

The averaging of five, or any number, of different quality scores may be a fractional value. However, because the quality scores are represented as rank-ordered integers, any fractional results may be accounted for by rounding s up or down to the nearest integer. This creates an error probability $P_s$ for the base call at position i that is determined by the sum of the average deletion, insertion, and substitution error probabilities for all of the base calls within a window of size 5 centered on the base call at position i.

The axis in FIG. 8 are the same as in FIG. 4. The error probability is much higher for the lower quality labels, there is an artifact around quality label 35, and there is a large amount of noise affecting the error probabilities for the higher quality labels. Using the techniques described above of calculating error probability from the average of a window of base calls provides an improvement over the technique shown in FIG. 4 which evaluates each base call in isolation. In graph 800, the lowest error probability is 0.063 while in graph 400 is slightly higher at 0.067. Techniques described in association with graph 400 in FIG. 4 such as binning or grouping quality labels and assigning the lowest error probability to the higher quality labels may also be applied in the same manner to graph 800.

Figure 9:
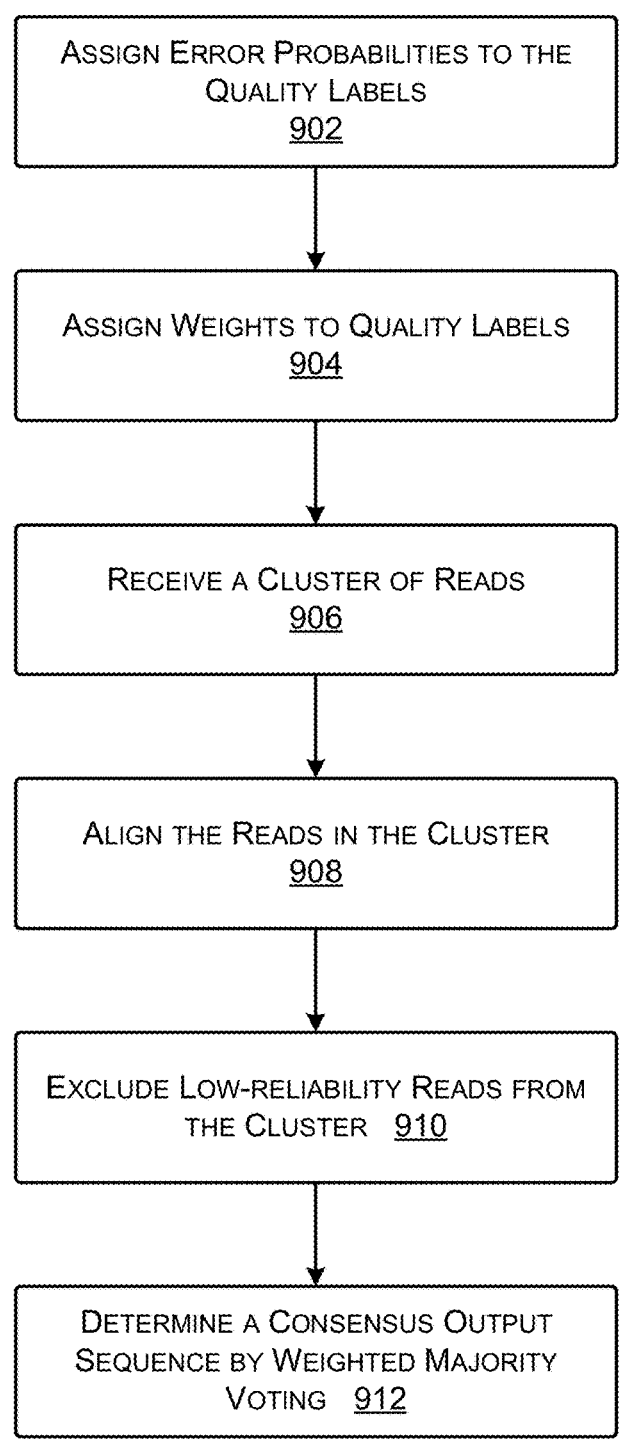
FIG. 9 shows an illustrative process for determining a consensus output sequence by weighted majority voting.

FIG. 9 shows process 900 for determining a consensus output sequence by weighted majority voting. Process 900 may be performed by the trace reconstruction system 102 shown in FIGS. 1 and 2.

At operation 902, error probabilities are assigned to quality labels based on empirical error data obtained from sequencing a set of multiple test polymers with known sequences. The set of test polymers may include many thousands, tens-of-thousands, hundreds-of-thousands or more individual polymers. The empirical error data may indicate a number of errors in terms of substitutions, deletions, insertions, and total errors. The number of errors (e.g., the number of total errors) may be used to determine an error rate or percentage. The error probabilities may be derived from empirical error data such as illustrated in FIGS. 4 and 8. This operation may be omitted if the quality labels represent error probabilities or if the quality labels have previously been associated with quality labels.

At operation 904, weights are assigned to the quality labels. The weights are based on the error probabilities associated with each of the quality labels. The weights may be the probability that a read symbol with a given quality label is correct. For example, a quality symbol that is associated with a 10% error rate may have a 0.9 probability of being accurate and the weight would then be 0.9. Error probabilities may be converted into weights in any number of different ways such as by weighing a read symbol s in the reads by $\log((1-P_S)/P_S)$, wherein Ps is the error probability assigned to a quality label associated with the read symbol s.

At operation 906, a cluster of reads is received. Multiple reads are grouped into a cluster based on a likelihood of the reads being derived from a same polymer. Thus, any variation in the reads would be most likely due to errors introduced by sequencing. A cluster may include from 1 to as many as 100 or more reads. In some instances, a cluster may include between 5 and 15 reads. The cluster of reads may be received from the output of analysis (i.e., clustering) of sequencer output. Process 900 may be repeated for some or all of the clusters produced from a single sequencing run.

At operation 908, the reads in the cluster are aligned. Alignment positions the reads in the cluster so that all read symbols that likely represent the same monomer subunit of the polymer are positioned for comparison to each other. This alignment spans the reads in the cluster. Individual reads that do not have a read symbol at the position of comparison (e.g., due to a deletion or different length reads) may have an empty value at this position. Many suitable techniques for multiple sequence alignment are known to persons of ordinary skill in the art.

At operation 910, low-reliability reads are excluded from the cluster. A low-reliability read may be excluded from the cluster of reads based on its overall reliability. Overall reliability is the probability of the entirety of the read being correct. This may be calculated by multiplying the probability of each read symbol being correct (i.e., product of $1-P_{s_i}$ where $s_i$ represents the error probability of $i^{th}$ read symbol).

In some implementations all reads with an overall reliability below a cutoff threshold are omitted. In other implementations, the read with the lowest overall reliability is omitted without regard to a threshold (e.g., in a cluster that contains only two reads). This operation may also be omitted regardless of overall reliability.

At operation 912, a consensus output sequence is determined by weighted majority voting. The weights assigned to the quality labels at 904 are used to weigh each read symbol according to its associated quality label. In some implementation, a read symbol is weighted based on error probabilities of adjacent read symbols in a window that includes the read symbol. The window may be centered around the read symbol and include one, two, three, or more read symbols on either side. The error probabilities for all the read symbols in the window may be averaged and this average value is assigned to the read symbol as its error probability. Process 900 differs from unweighted majority voting because it uses error probabilities to give more weight to read symbols that are more likely to be accurate and less weight to read symbols that are less likely to be accurate. This can produce a more accurate consensus output sequence than ignoring quality label data.

Figure 10:
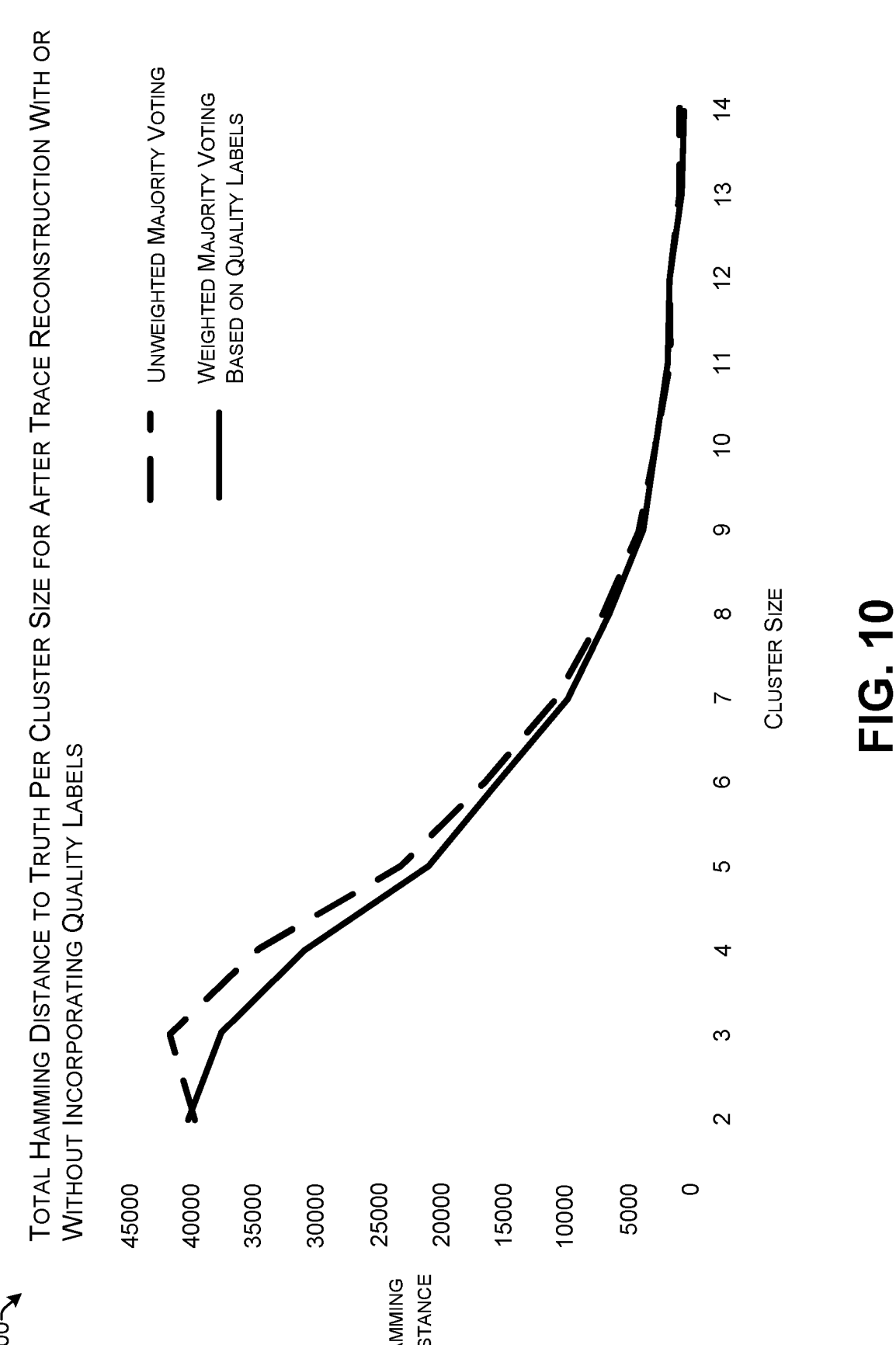
FIG. 10 is a graph showing improvements in the accuracy of consensus output sequences generated using weighted majority voting according to the techniques of this disclosure relative to using unweighted majority voting.

FIG. 10 is a graph 1000 showing how weighted majority voting based on quality labels improves accuracy of trace reconstruction for clusters including three to eight reads. Graph 1000 shows total Hamming distance to truth per cluster size for trace reconstruction using unweighted majority voting (upper line) and using weighted majority voting based on quality labels (lower line) to determine a consensus output sequence. Hamming distance between two reads of equal length is the number of positions at which the corresponding read symbols are different. Thus, Hamming distance measures the minimum number of substitutions required to change one read into the other or the minimum number of substitution errors that could have transformed one read into the other.

A Hamming distance of zero indicates that the consensus output sequence is the same as the actual DNA strand. Larger Hamming distances indicate greater error. The data shown in FIG. 10 was generated by Nanopore sequencing of DNA strands with known sequences which provide the "truth" to which consensus output sequences are compared. The total Hamming distance shown on the vertical axis is the sum of all the Hamming distances for the consensus output sequences generated from clusters of the size indicated on the horizontal axis.

The weights used for the weighted majority voting were determined for each position in the consensus output sequences individually without considering the quality labels for adjacent positions. The weights were calculated from error probabilities by $\log(1-P_S/P_S)$, wherein $P_s$ is the error probability assigned to a quality label associated with base call s.

Table 3 below shows the data used to create FIG. 10 in tabular form. Size indicates the number of DNA reads in a cluster. Count indicates the number of clusters generated from the sequence data of a given size. The distance gain is the difference between the hamming score from consensus output sequences determined by unweighted majority voting and the hamming scores from consensus output sequences determined by weighted majority voting. A positive distance gain indicates a lower Hamming score and improved accuracy.

TABLE 3

Hamming distance to truth per cluster size for Nanopore
sequencing output after trace reconstruction with
or without incorporating quality labels.

| | | Average Hamming Distance Per Read | | |
| Size | Count | Without Quality Labels | With Quality Labels | Distance Gain |
|---|---|---|---|---|
| 1 | 620 | 39.05 | 39.05 | 0 |
| 2 | 1307 | 30.49502678 | 30.68859985 | −0.193573068 |
| 3 | 2246 | 18.54942119 | 16.81834372 | 1.731077471 |
| 4 | 3498 | 9.88593482 | 8.840480274 | 1.045454545 |
| 5 | 4502 | 5.18080853 | 4.645713016 | 0.535095513 |
| 6 | 5420 | 3.059409594 | 2.832472325 | 0.226937269 |

TABLE 3-continued

Hamming distance to truth per cluster size for Nanopore
sequencing output after trace reconstruction with
or without incorporating quality labels.

| | | Average Hamming Distance Per Read | | |
| | | --- | --- | |
| Size | Count | Without Quality Labels | With Quality Labels | Distance Gain |
| --- | --- | --- | --- | --- |
| 7 | 6382 | 1.686775306 | 1.542306487 | 0.144468819 |
| 8 | 6994 | 1.00486131 | 0.923934801 | 0.080926508 |
| 9 | 6943 | 0.570214605 | 0.524413078 | 0.045801527 |
| 10 | 7031 | 0.4071967 | 0.386431518 | 0.020765183 |
| 11 | 6839 | 0.237315397 | 0.242871765 | −0.005556368 |
| 12 | 6519 | 0.250191747 | 0.241908268 | 0.008283479 |
| 13 | 5870 | 0.144463373 | 0.128109029 | 0.016354344 |
| 14 | 5455 | 0.14243813 | 0.105957837 | 0.036480293 |
| 15 | 4768 | 0.118917785 | 0.118917785 | 0 |
| 16 | 4298 | 0.075616566 | 0.084690554 | −0.009073988 |
| 17 | 3775 | 0.062251656 | 0.034172185 | 0.02807947 |
| 18 | 3033 | 0.043850973 | 0.040883614 | 0.002967359 |
| 19 | 2653 | 0.050508858 | 0.041839427 | 0.008669431 |
| 20 | 2213 | 0.006326254 | 0.003615002 | 0.002711252 |

Graph 1000 and Table 3 show that Hamming scores decrease as cluster size increases. This is intuitively reasonable as a larger number of DNA reads minimizes the effect of errors in any single read. Majority voting of any variety is not applicable to clusters of size one because these clusters contain only a single DNA read. For clusters of size two, considering the effect of quality labels actually decreases accuracy by a small amount. This result may be different for other data sets.

The improvement provided by using quality labels to create weights for majority voting is most pronounced for clusters of size three to eight. There are also small improvements for clusters of size nine and 10. For cluster sizes greater than 10 the difference is very small or even negative likely due to noise. The lack of improvement for larger cluster sizes is likely because the consensus output sequences identified for these clusters are already highly accurate (due to the benefits of averaging errors over a larger set of reads) even without accounting for quality labels. Unweighted majority voting may be used for cluster sizes greater than eight, greater than nine, or greater than 10 and achieve approximately the same results while avoiding the additional computation burden, processor usage, and memory consumption that comes with applying weights to majority voting.

Figure 11:
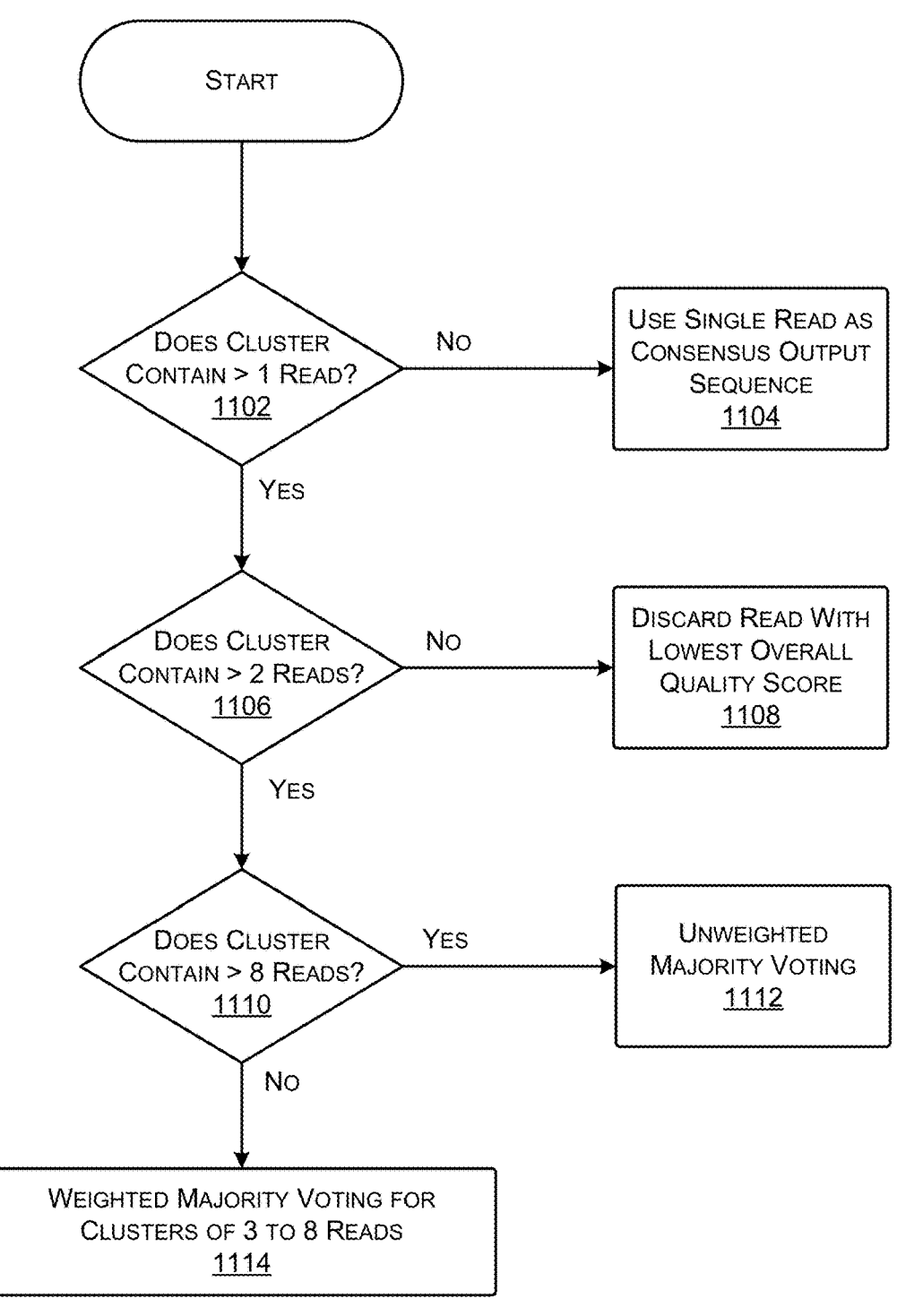
FIG. 11 shows an illustrative process for determining when to use weighted majority voting based on cluster size.

FIG. 11 shows process 1100 for selecting a trace reconstruction technique based on cluster size. The data shown in FIG. 10 and Table 2 indicates that cluster size can affect the performance of trace reconstruction techniques. Process 1100 may be applied to any set of sequencer outputs grouped into one or more clusters. In some implementations, a single sequencing run will generate a large set of reads that are clustered in many thousands or tens-of-thousands of clusters. Process 1100 may be applied to each cluster as one way of determining which trace reconstruction technique to use.

At operation 1102, it is determined if the cluster contains more than one read. If not and the cluster contains only one read, process 1100 proceeds along the "no" path to 1104 and the single read is used as the consensus output sequence. But if there are more than one read in the cluster, process 1100 proceeds along the "yes" path to 1106.

At operation 1106, it is determined if the cluster contains more than two reads. If not, and the cluster contains two reads, process 1100 proceeds along the "no" path to 1108.

At operation 1108, one of the two reads with the lowest overall quality score is discarded. The remaining read is then used as the consensus output sequence. This is an example of a hard bias that completely excludes one or more reads based on low overall quality scores. The data in Table 2 indicates that for clusters of size two, using weighted majority voting does not improve accuracy. Unweighted majority voting will result in any position at with the two reads differ as being ambiguous because there are two equally weighed votes for different read symbols. Discarding the lowest quality read is also more computationally efficient than performing weighted majority voting.

If, at operation 1106, it is determined that there are more than two reads (i.e., at least three reads) in the cluster, then process 1100 proceeds along the "yes" path to 1110. At operation 1110, it is determined if the cluster contains more than eight reads. Eight reads is identified in Table 2 and FIG. 10 as the largest cluster size at which weighted majority voting provides increased accuracy. However, the number eight may be replaced with another upper threshold number such as, but not limited to, nine or 10. If the cluster contains more than eight reads, process 1100 proceeds along the "yes" path to 1112.

At operation 1112, trace reconstruction is performed with unweighted majority voting. Table 2 and FIG. 10 show that weighted and unweighted majority voting provide similar results for clusters of size nine or larger. Although weighted majority voting could be performed for clusters that include more than eight reads, there is a computational cost to adding weights to majority voting. Avoiding this cost when there is no benefit saves processor cycles and memory usage.

If, at operation 1110, it is determined that there are eight or fewer reads in the cluster (e.g., a cluster size of 3-8) then process 1100 proceeds along the "no" path to 1114. At operation 1114, trace reconstruction is performed using weighted majority voting according to any of the techniques provided in this disclosure.

Figure 12:
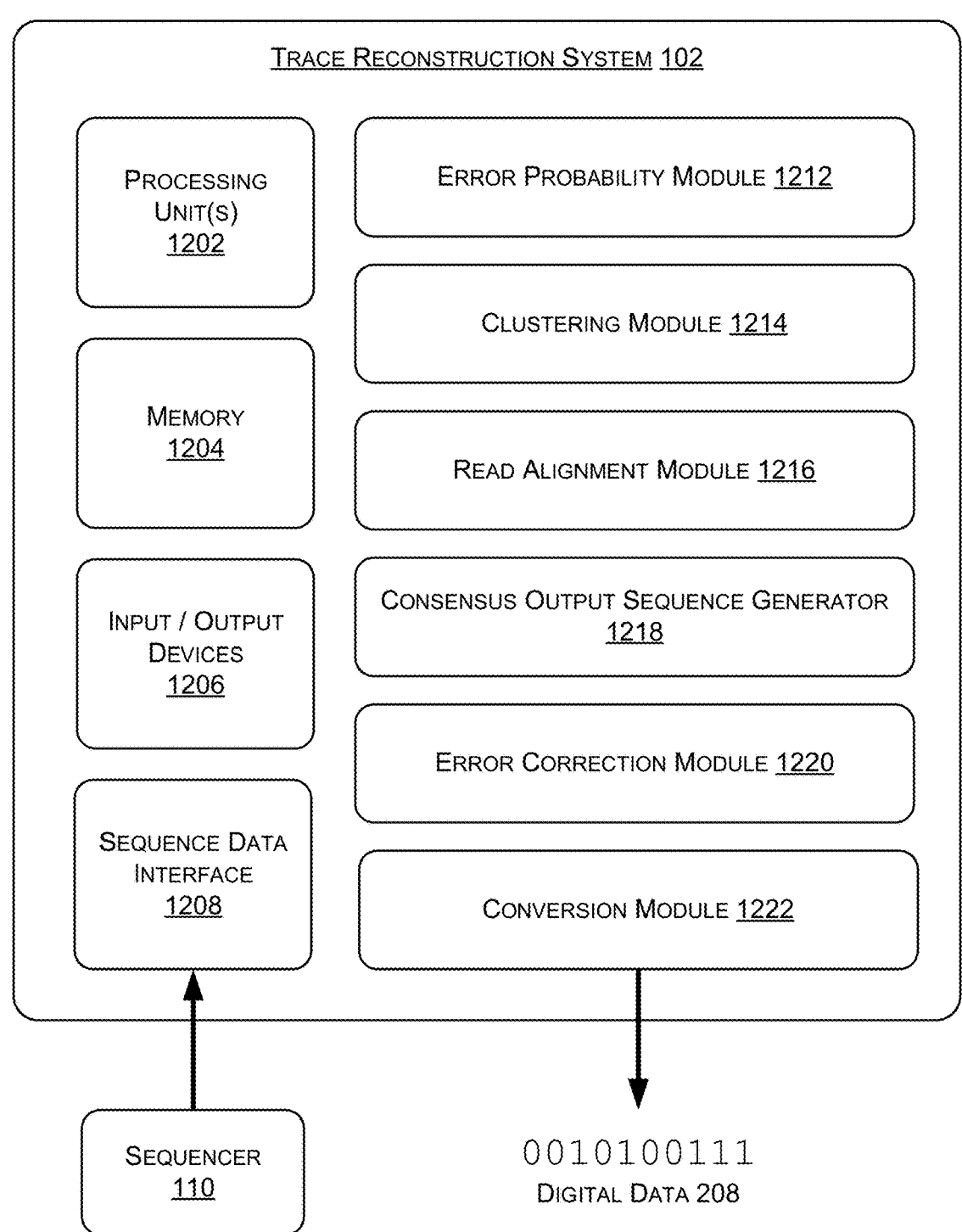
FIG. 12 shows a block diagram of an illustrative trace reconstruction system.

FIG. 12 shows an illustrative block diagram 1200 of the trace reconstruction system 102 shown in FIG. 1. Recall that the trace reconstruction system 102 may be implemented in whole or in part in any of the computing device 118, the sequencer 110, and the servers 120. Thus, the trace reconstruction system 102 may be implemented in a system that contains one or more processing unit(s) 1202 and memory 1204, both of which may be distributed across one or more physical or logical locations. The processing unit(s) 1202 may include any one or more type of processors such as central processing units (CPUs), graphical processing units (GPUs), single-core processors, multi-core processors, application-specific integrated circuits (ASICs), programmable circuits such as Field Programmable Gate Arrays (FPGA), and the like. One or more of the processing unit(s) 1202 may be implemented in software and/or firmware in addition to hardware implementations. Software or firmware implementations of the processing unit(s) 1202 may include computer- or machine-executable instructions written in any suitable programming language to perform the various functions described. Software implementations of the processing unit(s) 1202 may be stored in whole or part in the memory 1204.

Alternatively, or additionally, the functionality of the trace reconstruction system 102 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (AS- SPs), System-on-a-chip systems (SOCs), Complex Programmable Logic Devices (CPLDs), etc. Implementation as hardware logic components may be particularly suited for portions of the trace reconstruction system 102 that are included as on-board portions of the sequencer 110. The trace reconstruction system 102 may also include one or more input/output devices 1206 such as a keyboard, a pointing device, a touchscreen, a microphone, a camera, a display, a speaker, a printer, and the like.

Memory 1204 of the trace reconstruction system 102 may include removable storage, non-removable storage, local storage, and/or remote storage to provide storage of computer-readable instructions, data structures, program modules, and other data. The memory 1204 may be implemented as computer-readable media. Computer-readable media includes at least two types of media: computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology. Computer-readable storage media also includes CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer-readable instructions, data structures, program modules, or other data in a modulated data signal, such as a carrier wave, or other transmission mechanism. As defined herein, computer-readable storage media and communications media are mutually exclusive.

The trace reconstruction system 102 may be connected to one or more sequencers 110 through a direct connection and/or a network connection by a sequence data interface 1208. The direct connection may be implemented as a wired connection, a wireless connection, or both. The network connection may include the network 122. The sequence data interface 1208 receives one or more reads from the sequencer 110. The reads may be provided as FASTQ files or in another format.

The trace reconstruction system 102 includes multiple modules that may be implemented as instructions stored in the memory 1204 for execution by processing unit(s) 1202 and/or implemented, in whole or in part, by one or more hardware logic components or firmware.

An error probability module 1212 identifies error probabilities for quality labels provided by the sequencer 110. Quality labels provided by some sequencers may include a probability of error such as Phred or Q scores provided by Illumina® sequencers. Other sequencers provided quality labels that represent relative quality levels without a direct correlation to error probability.

If quality labels are not correlated with error probabilities, such as with output from Nanopore sequencers, the error probability module 1212 may access a table or function that correlates individual quality labels with error probabilities. Error rate data used for correlating quality labels with error probabilities may be based on empirical testing of a sequencer. The empirical testing may be specific for a class of sequencers such as all nanopore sequencers, a particular model of sequencer such as Oxford Nanopore MinION® sequencer, or an individual machine. If multiple sets of error rate data are available, the error probability module 1212 may select the most specific data (e.g., for the individual machine rather than for a class of sequencers), the most recent data, or may use a data set manually selected by a user.

A clusterization module 1214 clusters a subset of the plurality of reads based on a likelihood of the subset of the plurality of reads being derived from the same polymer. Data received at the sequence data interface 1208 from the sequencer 110 may contain a set of reads generated from each polymer provided to the sequencer 110. Although there may be errors in many of the reads, the reads of the same polymer are generally more similar to each other than they are to reads from a different polymer.

Further analysis would be hampered if the set of reads to be analyzed includes reads of different polymers. Thus, clustering may be performed in order to limit the data for further analysis to a subset of the reads that likely represent the same polymer. A poorly formed cluster may be "poorly" formed due to over or under inclusion. An overly inclusive, poorly formed, cluster is one that groups reads of more than one polymer in a single cluster. An underinclusive, poorly formed, cluster is one of multiple clusters that should be grouped into a single large cluster but instead are divided into multiple smaller clusters.

The clusterization module 1214 can use any suitable clustering technique such as connectivity-based clustering (e.g., hierarchical clustering), centroid-based clustering (e.g., k-means clustering), distribution-based clustering (e.g., Gaussian mixture models), density-based clustering (e.g., density-based spatial clustering of applications with noise (DBSCAN)), etc. The trace reconstruction system 102 may analyze one or more, including all, of the clusters derived from the data output by the sequencer 110. As mentioned above, the number of reads in a cluster may depend on the depth of sequencing. With Nanopore sequencing, there may be between about 1 to 100 reads, 3 to 25 reads, or 5 to 15 reads per cluster.

A read alignment module 1216 aligns the plurality of reads at a position of comparison spanning the plurality of reads. In one implementation, the left ends of the reads (e.g., corresponding to the 5' ends of DNA strands) may be aligned. Alternatively, the right ends of the reads (e.g., corresponding to the 3' ends of DNA strands) may be aligned. This first position in the reads may be used as the initial position of comparison. As analysis proceeds, the read alignment module 1216 moves the position of comparison along each read a number of positions. Multiple sequence alignment techniques are known to those of ordinary skill in the art. Example techniques are implemented by sequence alignment software such as multiple variations of Clustal and T-coffee.

Alignment of the reads may be shifted relative to each other based on detection of deletions or insertions. The shifting of the alignment keeps the remaining positions in the reads in phase with each other by accounting for additional or missing read symbols. In one implementation, the read alignment module 1216 advances the position of comparison by one position for reads that have the plurality consensus base call at the position of comparison, by one position for a variant read if the error type is classified as substitution, by zero positions for a variant read if the error type is classified as deletion, or by two positions for a variant read if the error type is classified as insertion.

A consensus output sequence generator 1218 determines a consensus output sequence 204 based on the plurality consensus output read symbols identified by weighted majority voting and the alignment provided by the read alignment module 1216. Each position in the consensus output sequence 204 is the plurality consensus read symbol at that position in view of the weights based on error probabilities provided by the error probability module 1212. The consensus output sequence may be determined by any of the techniques for weighted majority voting described above and shown in FIG. 3.

In some implementations, the consensus output sequence generator 1218 may use different techniques for different cluster sizes as shown in FIG. 11. Specifically, for a cluster that includes only one read, that single read is used as the consensus output sequence. If the cluster includes less than a threshold number of reads (e.g., two or three reads), then the read with a lowest overall quality score is discarded and the consensus output sequence is determined from the remaining reads in the cluster. Also, if the cluster includes more than a threshold number of reads (e.g., seven, eight, or nine reads), then the consensus output sequence may be determined by unweighted majority voting. Omitting weighing when it does not provide increase accuracy improves operation of a computing system by reducing computational load which can decrease the number of processor cycles used and memory consumed.

An error correction module 1220 may apply additional error correction techniques to decode the consensus output sequence provided by the consensus output sequence generator 1218. In some implementations, the error correction module 1220 uses a non-binary error-correcting code to decode the consensus output sequence based on redundant data that is encoded into the polymers. Many types of non-binary error correction techniques are known to those of ordinary skill in the art. One example of this type of error correction is Reed-Solomon error correction. In an example implementation, a Reed-Solomon outer code may be added to the starting digital data and ultimately distributed across many polymers (e.g., 10,000-100,000 unique molecules) when stored.

It is possible that the Reed-Solomon error correction may fail to decode the consensus output sequence if there are more than a threshold number of errors. If this occurs, trace reconstruction may be repeated with a change in one of the parameters. Changing a parameter may result in a different consensus output sequence that the Reed-Solomon error correction is able to decode.

The use of error probabilities determined across a window of multiple read symbols rather than determined for each read symbol independent is one parameter that could be changed. The size of the window used to determine error probabilities is another variable that could be varied. A cut off threshold for overall reliability used to discard a read from a cluster could be also varied. After changing one or more parameters, it can be determined if the consensus output sequence generator 1218 produces a different consensus output sequence. If so, Reed-Solomon error correction may be applied to the new consensus output sequence. This may be repeated by making multiple different variations to the parameters until a consensus output sequence is generated that can be decoded by the Reed-Solomon error correction.

A conversion module 1222 converts the consensus output sequence into digital data 208. As described earlier, the digital data 208 may represent at least a portion of a digital file. The conversion from a series of read symbols (e.g., DNA base calls) to a string of digital data 208 is performed by reversing the operations that were originally used to encode the digital data 208. These operations will be known to the entity that operates the polymer storage 106. In some implementations, the converter 206 introduced in FIG. 2 may include the functionalities of the conversion module 1222 as well as the error correction module 1220. The digital data 208 may be used in the same manner as any other type of digital data. If the various error correction techniques are sufficient, the digital data 208 is identical to the original digital data.

Illustrative Embodiments

The following clauses describe multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of correcting base calling errors in oligonucleotide sequence data generated by a nanopore sequencer, the method comprising: receiving an output file generated by the nanopore sequencer, the output file comprising a plurality of oligonucleotide reads and associated quality labels for individual base calls in the plurality of oligonucleotide reads; assigning error probabilities to the quality labels based on empirical error data obtained from nanopore sequencing of a set of multiple test oligonucleotides with known sequences; clustering a subset of the plurality of oligonucleotide reads to create a cluster of oligonucleotide reads representing a same nucleotide; aligning the cluster of oligonucleotides reads at a position of comparison; and determining a consensus output sequence for the cluster of oligonucleotides reads by weighted majority voting of base calls in the oligonucleotides reads at the position of comparison, wherein weights used in the weighted majority voting are based on the error probabilities.

Clause 2. The method of clause 1, wherein the error probabilities are based on sums of deletion probabilities, insertion probabilities, and substitution probabilities.

Clause 3. The method of clause 1 or 2, wherein a base call s in the cluster of polynucleotide reads is weighted by $\log((1-P_S)/P_S)$, wherein $P_s$ is the error probability assigned to a quality label associated with the base call s.

Clause 4. The method of clause 1 or 2, wherein a base call in the cluster of polynucleotide reads is weighted based on an average of an error probability assigned to a quality label associated with the base call and the error probabilities assigned to quality labels associated with at least two adjacent base calls.

Clause 5. The method of any of clauses 1-4, further comprising: determining that the cluster of reads includes between three and eight polynucleotide reads and determining the consensus output polynucleotide sequence for the cluster of polynucleotides by weighted majority voting; and determining that an other cluster of reads includes less than three or more than ten polynucleotides reads and determining the consensus output polynucleotide sequence for the other cluster of polynucleotides reads by majority voting without error probability weighting.

Clause 6. The method of any of clauses 1-5, wherein a weight used for base calls associated with the lowest quality label or second lowest quality label is zero and a weight used for base calls associated with any of the top half of the quality labels is based on the lowest error probability of any quality label.

Clause 7. A method of correcting errors in sequence data generated by a sequencer, the method comprising: assigning error probabilities to quality labels; receiving a cluster of reads with associated quality labels for read symbols in the reads, the cluster comprising reads representing a same polymer; and determining a consensus output sequence for the cluster of reads by weighted majority voting of the read symbols with weights based on the error probabilities.

Clause 8. The method of clause 7, further comprising deriving the error probabilities for the quality labels based on empirical error data obtained from sequencing a set of multiple test polymers with known sequences.

Clause 9. The method of clause 7 or 8, further comprising clustering a plurality of reads based on a likelihood of the reads being derived from a same polymer thereby creating the cluster of reads.

Clause 10. The method of any of clauses 7-9, further comprising aligning the reads in the cluster of reads at a position of comparison spanning the reads, wherein the weighted majority voting is performed at the position of comparison and identifies a consensus output read symbol for the position of comparison.

Clause 11. The method of any of clauses 7-10, wherein a read symbol s in the reads is weighted by $\log((1-P_S)/P_S)$, wherein $P_s$ is the error probability assigned to a quality label associated with the read symbol s.

Clause 12. The method of any of clauses 7-11, further comprising, excluding a low-reliability read from the cluster of reads based on an overall reliability of the low-reliability read.

Clause 13. The method of any of clauses 7-12, wherein a read symbol of the read symbols is weighted based on error probabilities of adjacent read symbols in a window including the read symbol.

Clause 14. A system for correcting errors in sequence data generated by a sequencer, the system comprising: one or more processing units; a memory coupled to the one or more processing units; an error probability module stored in the memory and implemented on the one or more processing units to: assign error probabilities to quality labels provided by a sequencer; and a consensus output sequence generator stored in the memory and implemented on the one or more processing units to: receive a cluster of reads and associated quality labels for read symbols in the reads, the cluster comprising reads representing a polymer strand; and determine a consensus output sequence for the cluster of reads based on weighted majority voting of the read symbols weighted by the error probabilities.

Clause 15. The system of clause 14, wherein the error probability module is further implemented on the one or more processing units to derive the error probabilities for the quality labels based on empirical error data obtained from sequencing a set of multiple test polymers with known sequences.

Clause 16. The system of clause 14 or 15, further comprising a clustering module stored in the memory and implemented on the one or more processing units to cluster a plurality of reads based on a likelihood of the reads being derived from a same polymer thereby creating the cluster of reads.

Clause 17. The system of any of clauses 14-16, further comprising a read alignment module stored in the memory and implemented on the one or more processing units to align the reads in the cluster of reads at a position of comparison spanning the reads, wherein the consensus output sequence generator module performs the weighted majority voting at the position of comparison and identifies a consensus output read symbol for the position of comparison.

Clause 18. The system of any of clauses 14-17, wherein a read symbol of the read symbols is weighted by $\log((1-P_S)/P_S)$, wherein $P_s$ is the error probability assigned to the quality label associated with the read symbol.

Clause 19. The system of any of clauses 14-18, wherein the consensus output sequence module is further implemented on the one or more processing units to exclude a low-reliability read from the cluster of reads based on an overall reliability of the low-reliability read.

Clause 20. The system of any of clauses 14-19, wherein the error probability module is further implemented on the one or more processing units to determine an error probability for a read symbol based on error probabilities of adjacent read symbols in a window including the read symbol.

Clause 21. Computer-readable media encoding instructions which when executed by a processing unit cause a computing device to perform the method of any of clauses 1-13.

Clause 22. A system comprising a processing using and memory configured to implement the method of any of clauses 1-13.

Clause 23. A system for aligning of sequence reads comprising: one or more means for processing; a memory coupled to the one or more means for processing; means for assigning error probabilities to quality labels provided by a sequencer; a means for receiving a cluster of reads and associated quality labels for read symbols in the reads, the cluster comprising reads representing a polymer strand; and a means for determining a consensus output sequence for the cluster of reads based on weighted majority voting of the read symbols weighted by the error probabilities.

Clause 24. The system of clause 23, further comprising a means for clustering a plurality of reads based on a likelihood of the reads being derived from a same polymer thereby creating the cluster of reads.

Clause 25. The system of any of clause 23 or 24, further comprising a means for aligning the reads in the cluster of reads at a position of comparison spanning the reads, wherein the means for determining the consensus output sequence performs the weighted majority voting at the position of comparison and identifies a consensus output read symbol for the position of comparison.

Conclusion

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the," and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process or an alternate process. Moreover, it is also possible that one or more of the provided operations is modified or omitted.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A method of storing a digital file, the method comprising:
chemically synthesizing a pool of oligonucleotides having a sequence of nucleotide bases that encode original digital data which is the digital file;
sequencing the pool of oligonucleotides with a nanopore sequencer;
receiving an output file generated by the nanopore sequencer, the output file comprising a plurality of oligonucleotide reads and associated quality labels for individual base calls in the plurality of oligonucleotide reads, wherein the output file contains errors introduced by the nanopore sequencer;
assigning error probabilities to the associated quality labels based on empirical error data obtained from nanopore sequencing of a set of multiple test oligonucleotides with known sequences;
clustering a subset of the plurality of oligonucleotide reads to create a cluster of oligonucleotide reads representing a same nucleotide;
determining that the cluster of reads includes between three and eight oligonucleotide reads and determining a consensus output sequence for the cluster of oligonucleotides by weighted majority voting;
aligning the cluster of oligonucleotides reads at a position of comparison;
determining a consensus output sequence for the cluster of oligonucleotides reads by weighted majority voting of base calls in the oligonucleotides reads at the position of comparison;

determining that an other cluster of reads includes less than three or more than ten oligonucleotides reads and determining the consensus output sequence for the other cluster of oligonucleotides reads by majority voting without error probability weighting; and
converting the consensus output sequence into decoded digital data, wherein the decoded digital data is identical to the original digital data and encodes the digital file.

2. The method of claim 1, wherein the error probabilities are based on sums of deletion probabilities, insertion probabilities, and substitution probabilities.

3. The method of claim 1, wherein a base call in the cluster of oligonucleotide reads is weighted based on an average of an error probability assigned to a quality label associated with the base call and the error probabilities assigned to quality labels associated with at least two adjacent base calls.

4. The method of claim 1, wherein:
a weight used for base calls associated with a lowest quality label or a second lowest quality label is zero; and
a weight used for base calls associated with any of a top half of the associated quality labels is based on a lowest error probability of any quality label for the lowest quality half of the quality labels.

5. The method of claim 1, wherein a base call s in the cluster of polynucleotide reads is weighted by $\log((1-P_S)/P_S)$, wherein $P_s$ is the error probability assigned to a quality label associated with the base call s.

6. A method of recovering a digital file stored in a polymer pool, the method comprising:
sequencing the polymer pool with a sequencer, a sequence of monomers in the polymer pool encoding original digital data which is the digital file;
assigning error probabilities to quality labels;
receiving a cluster of reads with associated quality labels for read symbols in the reads, the cluster comprising reads representing a same polymer, wherein the reads contain errors introduced by a machine that performs the sequencing;
determining a number of reads in the cluster;
if the cluster of reads includes at least a first threshold number of oligonucleotide reads and no more than a second threshold number of oligonucleotide reads, determining a consensus output sequence for the cluster of reads by weighted majority voting of the read symbols with weights based on the error probabilities;
if the cluster of reads includes more than the second threshold number of reads, determining the consensus output sequence for the cluster of reads by majority voting without error probability weighting; and
converting the consensus output sequence into decoded digital data, wherein the decoded digital data is identical to the original digital data and encodes the digital file.

7. The method of claim 6, further comprising deriving the error probabilities for the quality labels based on empirical error data obtained from sequencing a set of multiple test polymers with known sequences.

8. The method of claim 6, further comprising aligning the reads in the cluster of reads at a position of comparison spanning the reads, wherein the weighted majority voting is performed at the position of comparison and identifies a consensus output read symbol for the position of comparison.

9. The method of claim 6, further comprising, excluding a low-reliability read from the cluster of reads based on an overall reliability of the low-reliability read, wherein a low-reliability read has overall reliability below a cutoff threshold or is a read with the lowest overall reliability in the cluster of reads.

10. The method of claim 6, wherein a read symbol of the read symbols is weighted based on error probabilities of adjacent read symbols in a window including the read symbol.

11. The method of claim 6, wherein a read symbol s in the reads is weighted by $\log((1-P_S)/P_S)$, wherein $P_S$ is the error probability assigned to a quality label associated with the read symbol s.

12. The method of claim 6, further comprising chemically synthesizing the polymer pool with the sequence of monomers that encode the digital file.

13. A system for storing a digital file in a polymer pool, the system comprising:

one or more processing units;

a memory coupled to the one or more processing units;

an error probability module stored in the memory and implemented on the one or more processing units to:

assign error probabilities to quality labels provided by a sequencer; and a consensus output sequence generator stored in the memory and implemented on the one or more processing units to:

receive a cluster of reads and associated quality labels for read symbols in the reads, the cluster comprising reads representing a polymer strand, wherein errors in the reads are introduced by the sequencer and a sequence of monomers in the reads encode original digital data which is the digital file;

determine a number of reads in the cluster;

if the cluster of reads includes at least a first threshold number of reads and no more than a second threshold number of reads, determine a consensus output sequence for the cluster of reads based on weighted majority voting of the read symbols weighted by the error probabilities; and if the cluster of reads includes more than the second threshold number of reads, determining the consensus output sequence for the cluster of reads by majority voting without error probability weighting; and a conversion module stored in the memory and implemented on the one or more processing units to convert the consensus output sequence into decoded digital data, wherein the decoded digital data is identical to the original digital data and encodes the digital file.

14. The system of claim 13, wherein the error probability module is further implemented on the one or more processing units to derive the error probabilities for the quality labels based on empirical error data obtained from sequencing a set of multiple test polymers with known sequences.

15. The system of claim 13, further comprising a clustering module stored in the memory and implemented on the one or more processing units to cluster a plurality of reads based on a likelihood of the reads being derived from a same polymer thereby creating the cluster of reads.

16. The system of claim 13, further comprising a read alignment module stored in the memory and implemented on the one or more processing units to align the reads in the cluster of reads at a position of comparison spanning the reads, wherein the consensus output sequence generator performs the weighted majority voting at the position of comparison and identifies a consensus output read symbol for the position of comparison.

17. The system of claim 13, wherein the consensus output sequence generator is further implemented on the one or more processing units to exclude a low-reliability read from the cluster of reads based on an overall reliability of the low-reliability read, wherein a low-reliability read has overall reliability below a cutoff threshold or is a read with the lowest overall reliability in the cluster.

18. The system of claim 13, wherein the error probability module is further implemented on the one or more processing units to determine an error probability for a read symbol based on error probabilities of adjacent read symbols in a window including the read symbol.

19. The system of claim 13, wherein a read symbol of the read symbols is weighted by $\log((1-P_S)/P_S)$, wherein $P_S$ is the error probability assigned to the quality label associated with the read symbol.

20. The system of claim 13, further comprising a synthesizer configured to synthesize the polymer pool according to instructions specifying the sequence of monomers that encode original digital data.

\* \* \* \* \*